United States Patent
Grinstaff et al.

(10) Patent No.: US 10,617,794 B2
(45) Date of Patent: Apr. 14, 2020

(54) MACROINITIATORS FOR HYDROPHILIC COATINGS ON LATEX AND APPLICATIONS THEREOF

(71) Applicants: TRUSTEES OF BOSTON UNIVERSITY, Boston, MA (US); BOSTON MEDICAL CENTER CORPORATION, Boston, MA (US)

(72) Inventors: Mark W. Grinstaff, Brookline, MA (US); Stacy L. Chin, Brookline, MA (US); Ruiqing Xiao, Boston, MA (US); Benjamin Goldman Cooper, Brookline, MA (US); Karen Buch, Westborough, MA (US); Ducksoo Kim, Dover, MA (US)

(73) Assignees: Trustees of Boston University, Boston, MA (US); Boston Medical Center Corporation, Boston, MA (US)

( * ) Notice: Subject to any disclaimer, the term of this patent is extended or adjusted under 35 U.S.C. 154(b) by 0 days.

(21) Appl. No.: 15/552,875

(22) PCT Filed: Feb. 22, 2016

(86) PCT No.: PCT/US2016/018874
§ 371 (c)(1),
(2) Date: Aug. 23, 2017

(87) PCT Pub. No.: WO2016/137864
PCT Pub. Date: Sep. 1, 2016

(65) Prior Publication Data
US 2018/0043066 A1 Feb. 15, 2018

Related U.S. Application Data

(60) Provisional application No. 62/119,468, filed on Feb. 23, 2015.

(51) Int. Cl.
| | | |
|---|---|---|
| *A61L 31/10* | (2006.01) | |
| *C09D 133/06* | (2006.01) | |
| *A61L 27/34* | (2006.01) | |
| *A61L 29/04* | (2006.01) | |
| *A61L 29/08* | (2006.01) | |
| *A61L 31/04* | (2006.01) | |
| *A61L 27/16* | (2006.01) | |
| *A61L 31/14* | (2006.01) | |
| *C08F 220/06* | (2006.01) | |
| *C08F 220/28* | (2006.01) | |
| *C08J 7/04* | (2020.01) | |
| *A61L 31/16* | (2006.01) | |
| *C08J 7/18* | (2006.01) | |

(52) U.S. Cl.
CPC ............ *A61L 31/10* (2013.01); *A61L 27/16* (2013.01); *A61L 27/34* (2013.01); *A61L 29/041* (2013.01); *A61L 29/085* (2013.01); *A61L 31/048* (2013.01); *A61L 31/049* (2013.01); *A61L 31/14* (2013.01); *A61L 31/16* (2013.01); *C08F 220/06* (2013.01); *C08F 220/28* (2013.01); *C08J 7/047* (2013.01); *C08J 7/18* (2013.01); *C09D 133/066* (2013.01); *A61L 2400/10* (2013.01); *A61L 2420/02* (2013.01); *A61L 2420/06* (2013.01); *C08J 2321/02* (2013.01); *C08J 2433/02* (2013.01); *C08J 2433/06* (2013.01); *C08L 2205/04* (2013.01)

(58) Field of Classification Search
None
See application file for complete search history.

(56) References Cited

U.S. PATENT DOCUMENTS

| | | | | |
|---|---|---|---|---|
| 4,100,309 A | * | 7/1978 | Micklus | A61F 2/06 427/2.28 |
| 4,729,914 A | | 3/1988 | Kliment | |
| 5,077,352 A | * | 12/1991 | Elton | A61L 29/085 525/409 |
| 5,458,114 A | * | 10/1995 | Herr | A61F 6/04 128/842 |
| 5,468,821 A | * | 11/1995 | Lucast | A61L 15/24 526/264 |
| 5,648,425 A | * | 7/1997 | Everaerts | C08F 220/18 525/100 |
| 5,804,610 A | * | 9/1998 | Hamer | B29B 13/022 522/182 |
| 6,096,369 A | * | 8/2000 | Anders | C08J 7/16 427/2.28 |
| 6,238,799 B1 | * | 5/2001 | Opolski | A61L 27/34 428/34.3 |

(Continued)

FOREIGN PATENT DOCUMENTS

| | | |
|---|---|---|
| CN | 101999954 A | 4/2011 |
| EP | 0521605 A2 | 1/1993 |

(Continued)

OTHER PUBLICATIONS

Lee et al. Carbohydrate Polymers 2000 41:197-205 (Year: 2000).*
Sperling Journal of Polymer Science Part A-2 1969 7:425-427 (Year: 1969).*
Anderson et al. Journal of Applied Polymer Science 1979 23:2453-2462 (Year: 1979).*
Lopergolo et al. Polymer 2003 44:6217-6222 (Year: 2003).*
Phinyocheep "Chemical modification of natural rubber (NR) for improved performance" in Chemistry, Manufacture and Applications of Natural Rubber Ed. Kohjiya et al. Cambridge:Woodhead Publishing Limited 2014 p. 68 and 98-99 (Year: 2014).*

(Continued)

*Primary Examiner* — Robert A Wax
*Assistant Examiner* — Caralynne E Helm
(74) *Attorney, Agent, or Firm* — Nixon Peabody LLP

(57) ABSTRACT

Provided herein are methods comprising the use of a macroinitiator and application protocols to apply a hydrophilic coating to latex, or natural rubber, and compositions resulting from such methods. This coating results in e.g., an increased sense of lubrication when in contact with water or an aqueous solution.

19 Claims, 13 Drawing Sheets

(56) References Cited

U.S. PATENT DOCUMENTS

| | | | |
|---|---|---|---|
| 6,441,092 B1 * | 8/2002 | Gieselman | A61L 15/58 525/191 |
| 7,696,259 B2 * | 4/2010 | Hanley | A61L 29/085 427/487 |
| 8,541,498 B2 | 9/2013 | Sandhu | |
| 2006/0081264 A1 | 4/2006 | Vera | |
| 2010/0159116 A1 | 6/2010 | Rindlav-Westling | |
| 2011/0060070 A1 | 3/2011 | Dias | |
| 2011/0123475 A1 | 5/2011 | Dias | |
| 2013/0085563 A1 * | 4/2013 | Stankus | A61L 31/041 623/1.15 |
| 2013/0138210 A1 | 5/2013 | Myung | |
| 2014/0039067 A1 | 2/2014 | Magnet | |

FOREIGN PATENT DOCUMENTS

| | | | |
|---|---|---|---|
| EP | 0860172 B1 | 6/2003 | |
| EP | 2305744 B1 | 8/2016 | |
| WO | 1995/012420 A1 | 5/1995 | |
| WO | 2004/07174 A2 | 9/2004 | |
| WO | 2006/105001 A2 | 10/2006 | |
| WO | 2007/065720 A2 | 6/2007 | |
| WO | 2008/012325 A2 | 1/2008 | |
| WO | WO-2009152591 A1 * | 12/2009 | A61F 6/04 |
| WO | 2010/042712 A1 | 4/2010 | |
| WO | 2013/079975 A1 | 6/2013 | |

OTHER PUBLICATIONS

Carlini et al. New Polymeric Materials 1987 1(1):63-83 (Year: 1987).*

Wathier et al., "A large-molecular-weight polyanion, synthesized via ring-opening metathesis polymerization, as a lubricant for human articular cartilage", J Am Chem Soc 135(13) 4930-4933 (2013).

* cited by examiner

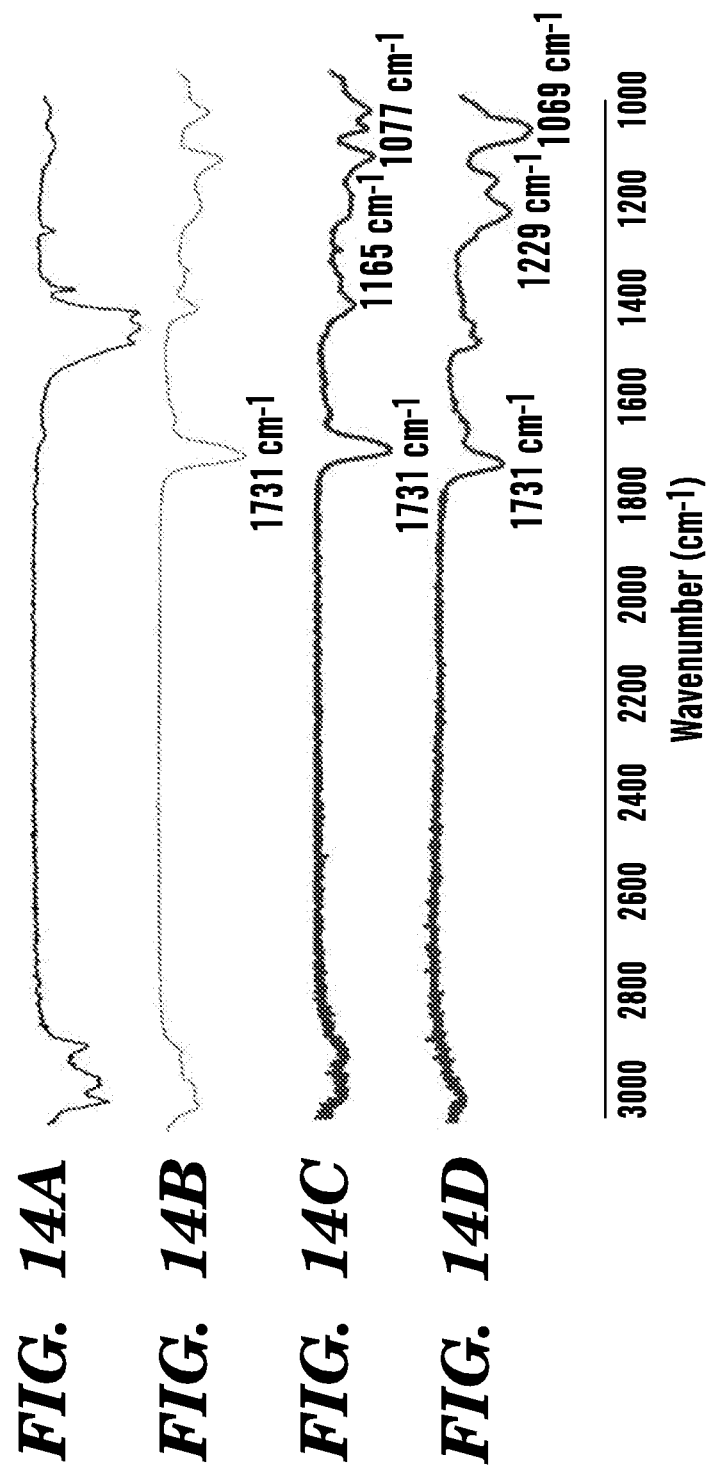

1

MACROINITIATORS FOR HYDROPHILIC COATINGS ON LATEX AND APPLICATIONS THEREOF

CROSS-REFERENCE TO RELATED APPLICATION

This Application is a 35 U.S.C. § 371 National Phase Entry Application of International Application No. PCT/US2016/018874 filed Feb. 22, 2016, which designates the U.S. and which claims benefit under 35 U.S.C. § 119(e) of the U.S. Provisional Application No. 62/119,468 filed Feb. 23, 2015, the contents of each of which are incorporated herein by reference in their entirety entireties.

FIELD OF THE DISCLOSURE

The field of the disclosure relates to methods for coating a latex article with a hydrophilic macroinitiator and compositions thereof.

BACKGROUND

Materials made from natural rubber, latex, or synthetic rubber possess ideal physical properties for various applications, including mechanical strength, low heat resistance, flexibility, and elasticity. Due to these advantages, natural rubber is commonly used in many commercially available products. Natural rubber is cultivated from *Hevea brasiliensis*, known as rubber trees, and is chemically composed of polymers with repeating units of isoprene (cis 1,4-polyisoprene). Its chemical composition and presence of unsaturated carbon-carbon double bonds contributes to natural rubber's hydrophobic nature, which can result in irreversible adsorption of biological components onto its surface. This limits the possibility of using natural rubber for in vivo applications and devices since latex is non-compatible with blood and can lead to bacterial, fungal, or protein accumulation on the surface.

Methods to modify the physical or chemical nature of natural rubber to possess hydrophilic properties are beneficial to expand the current application of latex to new materials, such as for in vivo devices. For example, guide wires and catheters coated with covalently-linked hydrophilic polymer coatings are used in interventional radiology and cardiology to reduce friction and abrasive forces between the body cavity and device interface. The application of a hydrophilic coating is advantageous for these types of medical devices because of the ability to reduce friction in conduits of the body, such as vascular, biliary, genitourinary and gastrointestinal systems, and to easily move within and traverse complex and tortuous anatomical terrains in viscous solutions, such as blood and bile. Decreasing friction and abrasive forces have resulted in lower complication rates from decreased microtrauma within the host environments and lower rates of infection by limiting aggregation of biological material on the catheter surface.

SUMMARY

The methods and compositions described herein are based, in part, on the discovery that a macroinitiator can be used in combination with a hydrophilic polymer in methods of coating latex articles to increase lubricity of the latex article. Accordingly, provided herein are latex articles comprising a hydrophilic polymer and a macroinitiating co-polymer that form an interpenetrating network on the surface of the latex. Also provided herein, are exemplary methods for coating such latex articles. In an exemplary embodiment, the latex article is a condom.

Lubricants are introduced to minimize mechanical and frictional stresses inflicted onto the latex condom surface and tissue interface to prevent condom breakage and to protect mucosal barriers from microtrauma while also increasing pleasure between partners during intercourse. Although condoms packaged with lubrication are commercially available, pre-lubricated condoms fail to provide sufficient lubrication throughout intercourse and can wear off after a short period of time. Therefore external lubrication must be applied to maintain the condom's lubricity and to minimize friction between the condom surface and tissue interface. However oil-based lubricants can weaken latex, limiting condoms to serve as prophylactic devices by preventing the exchange of bodily fluids between partners potentially putting users at risk for sexually transmitted infections (STIs). Although water- or silicone-based personal lubricants can avoid degradative activity upon latex, these types of lubricants can easily slough off from the sliding interface between the condom surface and tissue interface over repetitive cyclically articulations, such as that experienced during sexual intercourse.

In one aspect, provided herein is a composition comprising: a latex article having at least one layer of a hydrophilic coating, wherein the hydrophilic coating comprises a macroinitiating co-polymer and a hydrophilic polymer that form an interpenetrating co-polymer network on the surface of the latex article.

In one embodiment of this aspect and all other aspects described herein, the latex article is selected from the group consisting of male condoms, female condoms, latex-based gloves, biomedical devices, sexual stimulation devices, contact lenses, rubber bands, shoes, clothing, kitchen appliances, swimwear, sportswear, sporting instruments, boats, vehicles, military devices, or toys.

In another embodiment of this aspect and all other aspects described herein, the biomedical device comprises drug delivery devices, in vivo or in vitro diagnostic devices, medical catheters, balloons, stents, grafts, endoscopic devices, laparoscopic devices, electromedicine devices, or medical implants.

In another embodiment of this aspect and all other aspects described herein, the macroinitiating co-polymer is covalently linked to the latex article and the hydrophilic polymer is entangled within the macroinitiating co-polymer.

In another embodiment of this aspect and all other aspects described herein, the macroinitiating co-polymer comprises a randomized co-polymer.

In another embodiment of this aspect and all other aspects described herein, the macroinitiating co-polymer comprises one or more hydrophilic monomers that contain an acrylated, methacrylated, acrylamide, vinyl, or ethylenically unsaturated chemical group and a photosensitizer.

In another embodiment of this aspect and all other aspects described herein, the macroinitiating co-polymer comprises a Formula selected from the group consisting of Formulas A-H Formulas A-H.
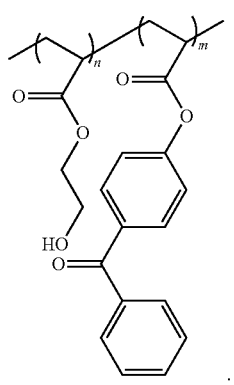
A
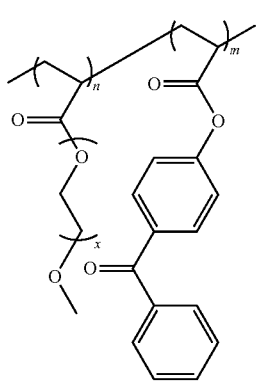
B
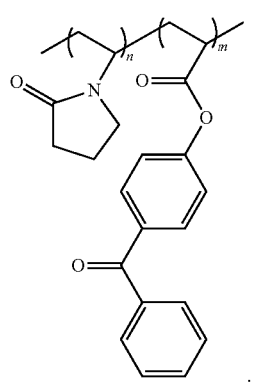
C
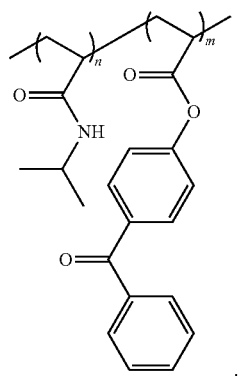
D
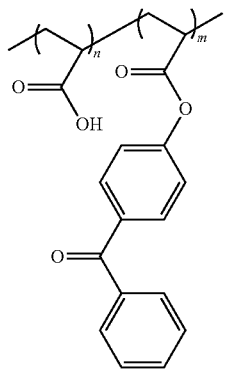
E
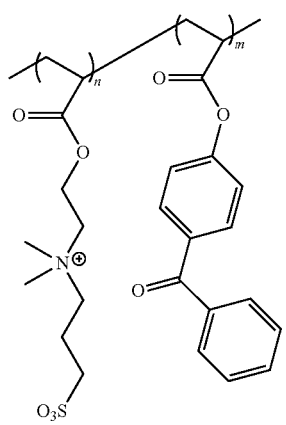
F
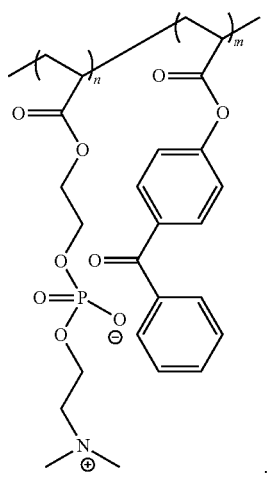
G

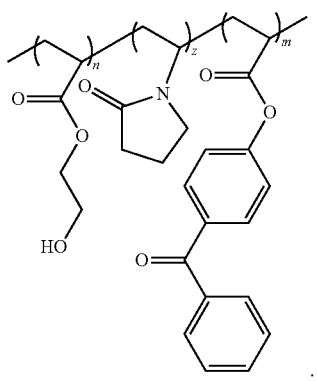

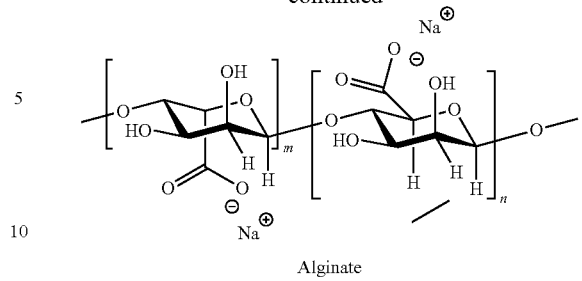

Alginate wherein:

n and m are integers that represent the number of randomized repeat unit in which n can range from 10 to 5000 and m can range from 1% to 50% w/w of "n".

In another embodiment of this aspect and all other aspects described herein, the randomized co-polymer comprises: (i) 2-hydroxyethylacrylate and a benzophenone polymer (HEA/BP) or (ii) acrylic acid and a benzophenone polymer (AA/BP).

In another embodiment of this aspect and all other aspects described herein, the macroinitiating polymer comprises a charged monomer, a zwitterionic monomer, a betaine monomer, or a carbohydrate or polysaccharide monomer.

In another embodiment of this aspect and all other aspects described herein, the hydrophilic polymer is selected from the group consisting of p(MPC)

p(PEG)

p(MA)

PVP

PVA

PEG and combinations thereof.

In another embodiment of this aspect and all other aspects described herein, the hydrophilic polymer is lightly cross-linked.

In another embodiment of this aspect and all other aspects described herein, the hydrophilic polymer comprises a molecular weight in the range of 2 k to 10000 k.

In another embodiment of this aspect and all other aspects described herein, the hydrophilic polymer comprises a thermoplastic polymer, a polysaccharide, or a charged hydrophilic polymer.

In another embodiment of this aspect and all other aspects described herein, the hydrophilic polymer is selected from the group consisting of polyvinypyrrilidone, poly(2-methacryloyloxyethyl phosphorylchlorine), polyethylene oxide, or polyethylene glycol.

In another embodiment of this aspect and all other aspects described herein, the composition further comprises at least one bioactive agent.

In another embodiment of this aspect and all other aspects described herein, the bioactive agent comprises an antimicrobial agent, an antibacterial agent, an antiretroviral agent, an antiviral agent, an antifungal agent, an anti-neoplastic/tumor agent, an anticoagulant, an antiplatelet agent, a thromboplastic agent, an anti-growth agent, a metallic nanoparticle, a growth agent, genetic or viral materials, a hormonal agent, a radioactive agent, a diagnostic imaging agent, a biosensor, or pharmaceutical formulations or combinations thereof.

In another embodiment of this aspect and all other aspects described herein, the hydrophilic coating is evenly distributed over the area of the latex article.

Another aspect provided herein relates to a method for coating a latex article with a hydrophilic coating, the method comprising: (a) contacting a latex article with a macroinitiating co-polymer and a hydrophilic polymer, (b) exposing the latex article to a light source, thereby coating the latex article with a hydrophilic coating.

In one embodiment of this aspect and all other aspects described herein, the latex article is selected from the group consisting of male condoms, female condoms, latex-based gloves, biomedical devices, sexual stimulation devices, contact lenses, rubber bands, shoes, clothing, kitchen appliances, swimwear, sportswear, sporting instruments, boats, vehicles, military devices, or toys.

In another embodiment of this aspect and all other aspects described herein, the biomedical device comprises drug delivery devices, in vivo or in vitro diagnostic devices, medical catheters, balloons, stents, grafts, endoscopic devices, laparoscopic devices, electromedicine devices, or medical implants.

In another embodiment of this aspect and all other aspects described herein, the macroinitiating co-polymer is covalently linked to the latex article and the hydrophilic polymer is entangled within the macroinitiating co-polymer.

In another embodiment of this aspect and all other aspects described herein, the macroinitiating co-polymer comprises a randomized co-polymer.

In another embodiment of this aspect and all other aspects described herein, the macroinitiating co-polymer comprises one or more hydrophilic monomers that contain an acrylated, methacrylated, acrylamide, vinyl, or ethylenically unsaturated chemical group and a photosensitizer.

In another embodiment of this aspect and all other aspects described herein, the macroinitiating co-polymer comprises a Formula selected from the group consisting of Formulas A-H Formulas A-H.

A
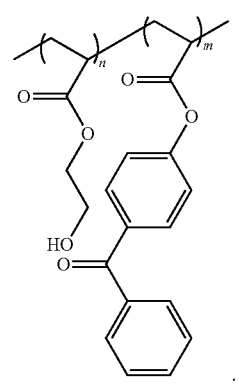

B
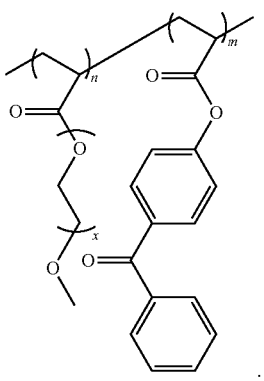

C
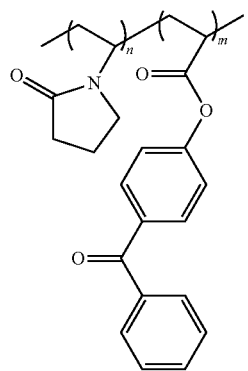

-continued

D
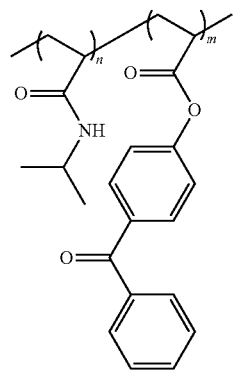

E
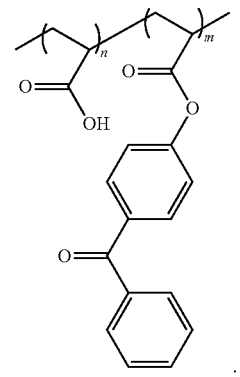

F
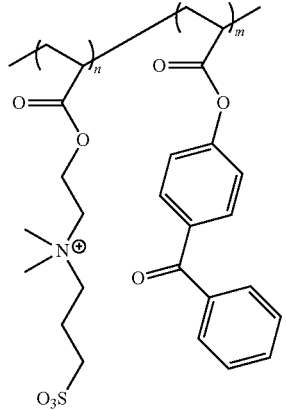

G
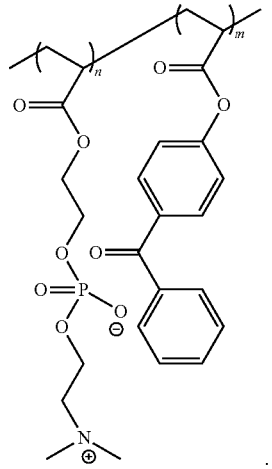

-continued

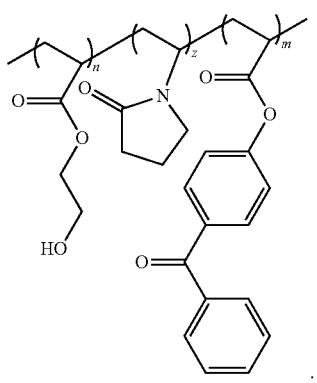

wherein:

n and m are integers that represent the number of randomized repeat unit in which n can range from 10 to 5000 and m can range from 1% to 50% w/w of "n".

In another embodiment of this aspect and all other aspects described herein, the randomized co-polymer comprises (i) 2-hydroxyethylacrylate and a benzophenone polymer (HEA/BP) or (ii) acrylic acid and a benzophenone polymer (AA/BP).

In another embodiment of this aspect and all other aspects described herein, the macroinitiating polymer comprises a charged monomer, a zwitterionic monomer, a betaine monomer, or a carbohydrate or polysaccharide monomer.

In another embodiment of this aspect and all other aspects described herein, the hydrophilic polymer is selected from the group consisting of

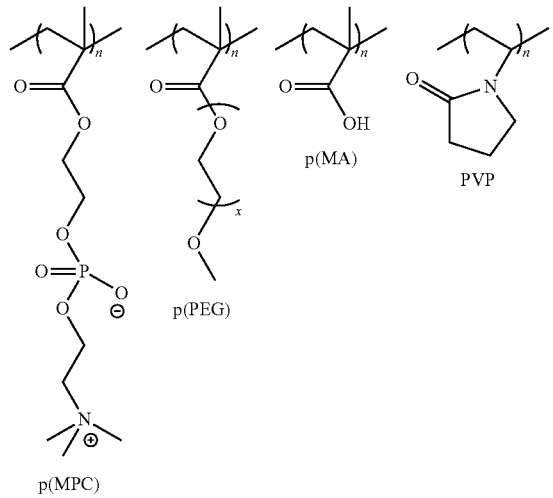

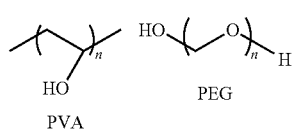

-continued

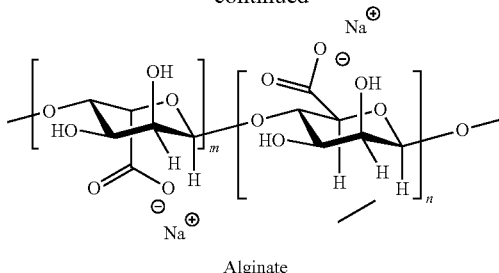

Alginate and combinations thereof.

In another embodiment of this aspect and all other aspects described herein, the hydrophilic polymer is lightly cross-linked.

In another embodiment of this aspect and all other aspects described herein, the hydrophilic polymer comprises a molecular weight in the range of 2 k to 10000 k.

In another embodiment of this aspect and all other aspects described herein, the hydrophilic polymer comprises a thermoplastic polymer, a polysaccharide, or a charged hydrophilic polymer.

In another embodiment of this aspect and all other aspects described herein, the hydrophilic polymer is selected from the group consisting of polyvinypyrrilidone, poly(2-methacryloyloxyethyl phosphorylchlorine), polyethylene oxide, or polyethylene glycol.

In another embodiment of this aspect and all other aspects described herein, wherein the coating further comprises a bioactive agent.

In another embodiment of this aspect and all other aspects described herein, the bioactive agent comprises an antimicrobial agent, an antibacterial agent, an antiretroviral agent, an antiviral agent, an antifungal agent, an anti-neoplastic/tumor agent, an anticoagulant, an antiplatelet agent, a thromboplastic agent, an anti-growth agent, a metallic nanoparticle, a growth agent, genetic or viral materials, a hormonal agent, a radioactive agent, a diagnostic imaging agent, a biosensor, or pharmaceutical formulations or combinations thereof.

In another embodiment of this aspect and all other aspects described herein, the hydrophilic coating is evenly distributed over the area of the latex article.

In another embodiment of this aspect and all other aspects described herein, the macroinitiating polymer is synthesized via a polymerization reaction.

In another embodiment of this aspect and all other aspects described herein, the polymerization reaction is initiated by a free radical initiator selected from the group consisting of an azo compound, an organic peroxide, an inorganic peroxide, and a redox initiating system.

In another embodiment of this aspect and all other aspects described herein, the polymerization reaction is initiated by a traditional free radical reaction, atom transfer radical polymerization, reversible addition-fragmentation chain transfer polymerization, cationic or anionic polymerization or a light source.

In another embodiment of this aspect and all other aspects described herein, the light source is selected from the group consisting of a lamp, a fiber optic device, a UV source, and a laser.

In another embodiment of this aspect and all other aspects described herein, the reaction time of the polymerization reaction is from 4 hr to 50 hr.

In another embodiment of this aspect and all other aspects described herein, the polymerization reaction is performed at a temperature between 75-100° C.

In another embodiment of this aspect and all other aspects described herein, the macroinitiating polymer is dissolved in one or more solvents.

In another embodiment of this aspect and all other aspects described herein, the hydrophilic polymer is lightly cross-linked by contacting the hydrophilic monomers with a cross-linking agent.

In another embodiment of this aspect and all other aspects described herein, the cross-linking agent is ethylene glycol diamethacrylate.

In another embodiment of this aspect and all other aspects described herein, the hydrophilic polymer is dissolved in solution at a range of 0.1% (w/v) to 10 (w/v) %.

In another embodiment of this aspect and all other aspects described herein, the solution further comprises a step of adding a thickening agent.

In another embodiment of this aspect and all other aspects described herein, the macroinitiating co-polymer and the hydrophilic polymer are applied to the latex article via electrochemical deposition, electrochemical plating, deposition from an aerosolized spray, a solvent evaporation method, a dip-coating method or by using a pipette to apply a thin, even layer onto a natural or synthetic rubber surface manually.

In another embodiment of this aspect and all other aspects described herein, the macroinitiating copolymer and the hydrophilic polymer are applied to the latex article via a spraying method.

In another embodiment of this aspect and all other aspects described herein, the latex article is pre-treated using a chemical modification process.

In another embodiment of this aspect and all other aspects described herein, the chemical modification process comprises a radical polymerization, an ionic polymerization, a photochemical initiation, a thermal initiation, a redox reactions, an argon plasma treatment or a vapor phase plasma treatment.

In another embodiment of this aspect and all other aspects described herein, further comprising a step of washing the coated latex article to remove excess macroinitiating co-polymer or hydrophilic polymer.

BRIEF DESCRIPTION OF THE DRAWINGS

FIG. 2A is an SEM image depicting a non-coated latex sample at 10 μm magnification. FIG. 2B is an SEM image depicting a treated latex sample coated with a solution of 5% (w/v) of HEA/BP at 10 μm magnification. FIG. 2C is an SEM image depicting a treated latex sample coated with a solution of 5% (w/v) of HEA/BP and 2% (w/v) of PVP at 10 μm magnification. FIG. 2D is an SEM image depicting a non-coated latex sample at 1 μm magnification. FIG. 2E is an SEM image depicting a treated latex sample coated with a solution of 5% (w/v) of HEA/BP at 1 μm magnification. FIG. 2F is an SEM image depicting a treated latex sample coated with a solution of 5% (w/v) of HEA/BP and 2% (w/v) of PVP at 1 μm magnification.

FIG. 4A is an SEM image depicting a non-coated latex sample at 1 μm magnification. FIG. 4B is an SEM image depicting a treated latex sample coated with a solution of 5% (w/v) of AA/BP at 10 μm magnification. FIG. 4C is an SEM image depicting a treated latex sample coated with a solution of 5% (w/v) of AA/BP and 2% (w/v) of PVP at 10 μm magnification.

FIG. 9A shows the complete torsion regimen and FIG. 9B shows the expanded view of initial 100 seconds of regimen.

FIGS. 13A-13C show Atomic Force Microscopy (AFM) images depicting the topography and roughness of latex samples coated with or without the hydrophilic coating. FIG. 13A, non-coated latex control; FIG. 13B, latex sample coated with the HEA/BP macroinitiator at 5 w/v % and 2 w/v % of PVP; and, FIG. 13C, latex sample coated with the AA/BP macroinitiator at 5 w/v % and 2 w/v % of PVP. An n=4 was conducted for all samples.

FIGS. 14A-14D show Fourier transform infrared spectroscopy (FT-IR) analysis of the HEA/BP macroinitiator treated on latex sheets with either the PEG or pMPC hydrophilic polymers. FIG. 14A shows FT-IR analysis of non-coated latex sheet; FIG. 14B shows FT-IR analysis of a latex sheet treated with a 5% w/v solution of the HEA/BP macroinitiator; FIG. 14C shows FT-IR analysis of a latex sheet treated with a 5% w/v solution of the HEA/BP macroinitiator and 2% w/v of PEG;

FIG. 14D shows FT-IR analysis of a latex sheet treated with a 5% w/v solution of the HEA/BP macroinitiator and 2% w/v of pMPC.

DETAILED DESCRIPTION

Figure 1:
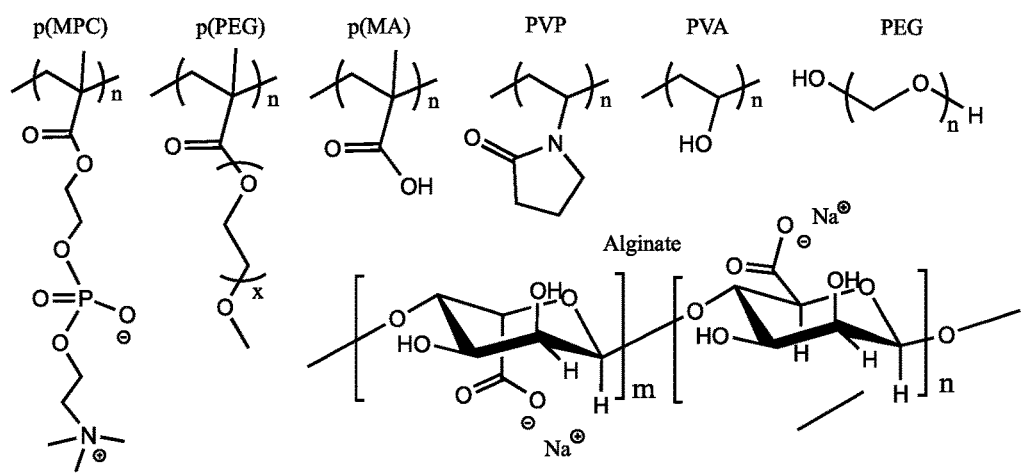
FIG. 1 depicts the chemical structures of various hydrophilic polymers such as p(MPC), p(PEG), p(MA), PVP, PVA, PEG, and alginate.

The application of a hydrophilic coating onto materials made from natural rubber, such as latex condoms, gloves, prosthetic devices, and catheters, affords these devices with the advantage of decreasing friction and abrasive forces especially when introduced into a physiological environment. For example, condoms made from natural rubber possess a hydrophobic nature, which can promote frictional and shearing forces at the condom surface and tissue interface, increasing the risk for condom breakage and mucosal microtrauma.

Provided herein are methods comprising the use of a macroinitiator and application protocols to apply a hydrophilic coating to latex, or natural rubber, and compositions thereof. This coating results in e.g., an increased sense of lubrication when in contact with water or an aqueous solution. The presence of the hydrophilic coating on treated latex-based materials reduces frictional and abrasive forces acting upon the surface, resulting in a "gliding sensation" when water is in contact with the coating instead. Additional advantages of the present invention include increasing the biocompatibility of natural rubber to blood as well as minimizing protein adherence and platelet adhesion onto its surface. The application of the hydrophilic coating permits the use of rubber and/or latex in biomedical devices.

Definitions

Unless stated otherwise, or implicit from context, the following terms and phrases include the meanings provided below. The definitions are provided to aid in describing particular embodiments, and are not intended to limit the claimed invention, because the scope of the invention is limited only by the claims. Further, unless otherwise required by context, singular terms shall include pluralities and plural terms shall include the singular. Thus, as used herein and in the claims, the singular forms include the plural reference and vice versa unless the context clearly indicates otherwise.

The singular terms "a," "an," and "the" include plural referents unless context clearly indicates otherwise. Similarly the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean 5% of the value being referred to. For example, about 100 means from 95 to 105.

As used herein, the term "latex article" refers to a composition comprising natural rubber latex, non-vulcanized rubber and/or synthetic latex. Typically, the latex article comprises a hydrophobic surface composed of e.g., a chemical composition of polyisoprene. In one embodiment, the latex is biocompatible (e.g., safe for use in human subjects), provided that the subject does not suffer from a latex allergy. As used herein, the term "biocompatible" refers to the absence of an adverse acute, chronic, or escalating biological response to an implant or coating, and is distinguished from a mild, transient inflammation which typically accompanies surgery or implantation of foreign objects into a living organism. Exemplary latex articles include, but are not limited to, condoms (both male and female), latex-based gloves, biomedical devices, sexual stimulation devices, contact lenses, rubber bands, shoes, clothing, kitchen appliances, swimwear, sportswear, sporting instruments, boats, vehicles, robotic devices, computer/electronic/electric devices, military devices, or toys. Non-limiting examples of latex biomedical devices include drug delivery devices (e.g., osmotic minipumps etc.), in vitro and in vivo diagnostic devices, medical implants (including e.g., cartilage substitutes, orthopedic joint replacement and resurfacing devices or components thereof, intervertebral discs, stents, heart valves, vascular grafts and the like), and vascular or urinary catheters.

The terms "macroinitiating co-polymer" and "macroinitiator" are used interchangeably herein and refer to a high molecular weight co-polymer comprising a randomized configuration of hydrophilic monomers and photosensitizer units.

As used herein, an "interpenetrating network" is a material comprising two or more polymer networks which are at least partially interlaced on a molecular scale, but not covalently bonded to each other, and cannot be separated unless chemical bonds are broken.

As used herein, the term "entangled" when used in reference to a hydrophilic polymer means that the polymer is trapped within the molecular network of the polymerized macroinitiating co-polymer, but is not covalently bound to the macroinitiator or the surface of the latex article. In one embodiment, the hydrophilic polymer cannot be removed from the interpenetrating network without breaking the chemical bonds of the polymerized macroinitiator.

As used herein, the term "lightly cross-linked" refers to a state of partial polymerization of the hydrophilic polymer, wherein less than the total number of available sites for cross-linking are cross-linked. For example, less than 90% of the sites are cross-linked; in other embodiments less than 80%, less than 70%, less than 60%, less than 50%, less than 40%, less than 30%, less than 20%, less than 15%, less than 10%, less than 5%, or less than 1% of the available sites are cross-linked. The term "lightly cross-linked" does not encompass the polymer where none of the available sites are cross-linked (i.e., unpolymerized polymer).

As used herein, the term "bioactive agent" refers to an agent that is capable of exerting a biological effect in vitro and/or in vivo. The biological effect can be therapeutic in nature. As used herein, "bioactive agent" can also refer to a substance that is diagnostic in nature. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, or polynucleotides.

As used herein, the term "pharmaceutically acceptable" refers to a formulation of a compound that does not significantly abrogate the biological activity, a pharmacological activity and/or other properties of the compound when the formulated compound is administered to a subject. In certain embodiments, a pharmaceutically acceptable formulation does not cause significant irritation to a subject.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzylphenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl, or heterocyclyl. Pharmaceutically acceptable solvates and hydrates are complexes of a compound with one or more solvent or water molecules, or 1 to about 100, or 1 to about 10, or one to about 2, 3, or 4, solvent or water molecules.

As used herein, the term "subject" refers to a human or an animal, typically a mammal, such as a cow, horse, dog, cat, pig, sheep, monkey, or other laboratory or domesticated animal. As used herein, the term "patient" includes human and animal subjects.

The phrase "therapeutically effective amount" refers to the amount of a pharmaceutical composition that elicits the biological or medicinal response in a tissue, system, animal, individual, patient, or human that is being sought by a researcher, veterinarian, medical doctor or other clinician.

As used herein, the terms "treating" or "treatment" encompass either or both responsive and prophylaxis measures, e.g., designed to inhibit, slow, or delay the onset of a symptom of a disease or disorder, achieve at least a partial reduction of a symptom or disease state, and/or to alleviate, ameliorate, or lessen, a disease or disorder and/or its symptoms. In one embodiment, treatment encompasses curing the disease.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Chemical Definitions

The term "MPC" means 2-methacryloyloxyethyl phosphorylcholine.

The term "pMPC" means poly(2-methacryloyloxyethyl phosphorylcholine).

The term "PEG" means poly(ethylene glycol).

The term "PEGDA" means poly(ethylene glycol) dimethacrylate.

The term "HEA" means 2-hydroxyethylacrylate.

The term "AA" means acrylic acid.

The term "BP" means benzophenone.

The term "PVP" means poly(vinylpyrrolidone).

The term "UV" means ultraviolet.

The term "IR" means infrared.

The term "SEM" means scanning electron microscopy.

The term "MW" means molecular weight.

The term "THEO" means theoretical.

The term "GPC" means gel permeation chromatography.

The term "FITC" means fluorescein isothiocyanate.

The term "DMEM" means Dulbecco's Modified Eagle Medium.

The term "COF" means coefficient of friction.

The tem "AIBN" means 2, 2'-azobis(2-methylpropionitrile).

The tem "THF" means tetrahydrofuran.

The term "(w/v)" means weight-to-volume.

The term "(w/w)" means weight-to-weight.

The term "k" means one-thousand or 1,000.

The term "wt" means weight.

The term "polysaccharide" refers to a compound that comprises at least two sugar units, or derivatives thereof. Polysaccharides may be purified from natural sources such as plants or may be synthesized de novo in the laboratory. Polysaccharides isolated from natural sources can be modified chemically to change their chemical or physical properties (e.g., reduced, oxidized, phosphorylated, crosslinked). Carbohydrate polymers or oligomers can include natural sugars (e.g., glucose, fructose, galactose, mannose, arabinose, ribose, xylose, etc.) and/or modified sugars (e.g., 2'-fluororibose, 2'-deoxyribose, etc.). Polysaccharides can also be either straight or branched. They can contain both natural and/or unnatural polysaccharide residues. The linkage between the residues can be the typical ether linkage found in nature or can be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "substituted", whether preceded by the term "optionally" or not, refers to the replacement of hydrogen radicals in a given structure with the radical of a specified substituent. When more than one position in any given structure can be substituted with more than one substituent selected from a specified group, the substituent can be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen can have hydrogen substituents and/or any permissible substituents of organic compounds described herein which satisfy the valencies of the heteroatoms.

The terms "natural rubber" and "latex" are used interchangeably within this disclosure. Both terms refer to the chemical compound cis 1,4-polyisoprene.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

While there is known and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

Macroinitiator Compositions

Surface grafting techniques are used to modify latex to obtain certain desired physical properties. UV-induced radical polymerization of hydrophilic monomers or low molecular weight hydrophilic polymers, such as methacrylated poly(ethylene glycol), N-vinyl pyrrolidone, 2-methacryloyloxyethyl phosphorylcholine, poly(ethylene glycol), poly(theyleneoxide), and poly(acrylamide) can effectively modify latex films to possess hydrophilic properties. However these approaches generally result in low grafting yields and the availability of different monomers capable of undergoing these particular reactions are limited. Latex can be pretreated with argon plasma or a vapor phase approach to improve grafting yields. However these pretreatment processes can easily damage latex if performed even under slightly harsh or unfavorable conditions.

An alternative approach to modify latex with hydrophilic properties and to increase the grafting yield on latex surfaces is to develop high molecular weight copolymers, termed macroinitiators, which are randomly composed of hydrophilic monomers and photosensitizer units. Increasing the molecular weight of the macroinitiator provides a greater amount of available initiation sites for the reaction to take place. The free radical polymerization is initiated when the photosensitizer is exposed to UV light, resulting in the abstraction of hydrogen atoms from latex and natural rubber (cis 1,4-polyisoprene), which is composed of unsaturated carbon-carbon double bonds. Without wishing to be bound by theory, this generates free radicals on the latex surface and promotes covalent bonds to form between the macroinitiator and the latex surface.

The macroinitiating polymer comprises one or more hydrophilic monomers that contain an acrylated, methacrylated, or ethylenically unsaturated group. As depicted in Formulas A-H, "n," "z," or "m" are integers which refer to the respective repeating unit of the co-polymer backbone, in which "n" or "z" is the integer corresponding to the hydrophilic monomer repeat number. "n" can varied from 10 to 5000, from 100 to 4000, from 200 to 3000, from 300 to 2000, or from 400 to 1000. "m" is integer corresponding to the photosensitizer, or photoinitiating monomer, repeat number, that can be varied from 1% to 50% (w/w) of "n." Varying the ratio of the photosensitizer to the hydrophilic monomer can affect the hydrophilicity of the overall macroinitiator since the photosensitizer unit may not be as water soluble as the hydrophilic monomer. In one embodiment, "m" can varied from a range of 1% (w/w) to 50% (w/w) of "n"; in other embodiments "m" can be varied from a range of 2% (w/w) to 40% (w/w) of "n", from 3% (w/w) to 30% (w/w) of "n", from 4% (w/w) to 20% (w/w) of "n", or from 5% (w/w) to 10% (w/w) of "n".

Formulae A-H.

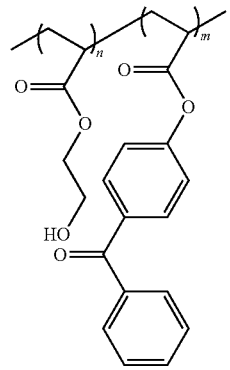

A

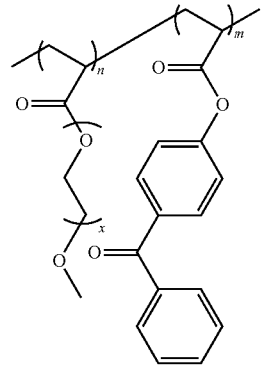

B

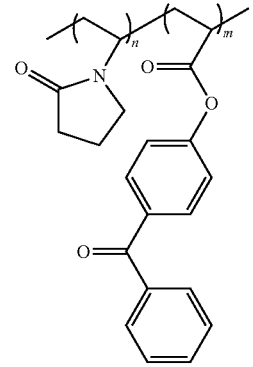

C

-continued

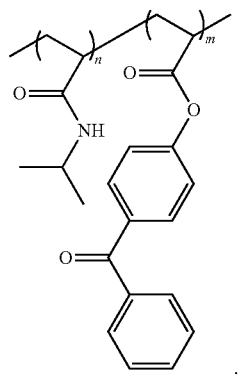

D

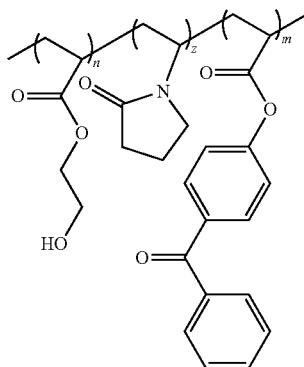

H

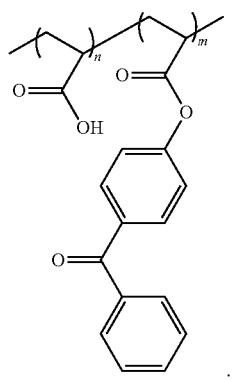

E  Formula I.

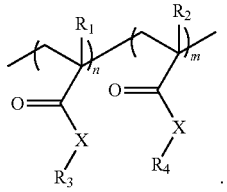

I

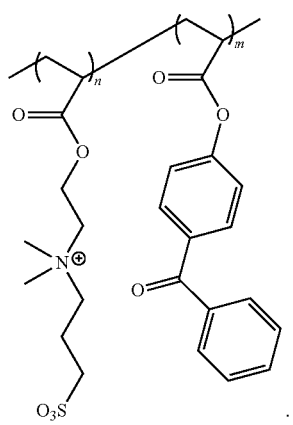

F

In some embodiments, X can be oxygen (O) or nitrogen (NH). In some embodiments, $R_1$ and $R_2$ can be a hydrogen, methyl, ethyl, or propyl group. In other embodiments $R_3$ can be hydrogen, sodium, potassium, 2-hydroxyethyl, 3-hydroxypropyl, 4-hydroxybutyl, 2-carboxyethyl, 3-carboxypropyl, 4-carboxybutyl, polyethylene glycol, isopropyl, 2-(trimethylammonium)ethyl, 3-(trimethylammonium)propyl, 2-(phosphorylcholine)ethyl, 3-sulfopropyl potassium salt, 2-(N-3-sulfopropyl-N,N-dimethyl ammonium)ethyl, 3-(N-3-sulfopropyl-N,N-dimethyl ammonium)propyl, 3-sulfopropyl potassium salt, or other water soluble acrylate, methacrylate, or ethylenically unsaturated monomers.

In some embodiments, the polymerizable group is a radically polymerizable group. Examples include, but are not limited to, acrylate, methacrylate, styrene, acrylamide, methacrylamide, ethyl acrylate, butyl acrylate, 2-ethylhexyl acrylate, hydroxyethyl acrylate, hydroxypropyl acrylate, carboxylethylacrylate, methylmethacrylate, ethyl methacrylate, butyl methacrylate, ethylhexyl methacrylate and decyl methacrylate, maleate, fumarate, and itaconate. In certain embodiments, other vinyl monomers include acrylic or vinyl acids and esters such as methacrylic acid, maleic acids, vinyl ether, allyl ether, alley ester, and vinyl ester, vinyl acetate, vinyl butyral. In some embodiments, the hydrophilic monomer can also be an acrylated or methacrylated sugar molecule, or any derivative thereof. Examples include, but are not limited to, methacrylated glucose, glucuronic acid, galactose, and similar structures that contain sulfate, carboxylate, phosphate, amine, and acetyl substitutions. Generally, any monomer possessing a polymerizable group can be used in the compositions, polymers, and methods as disclosed herein.

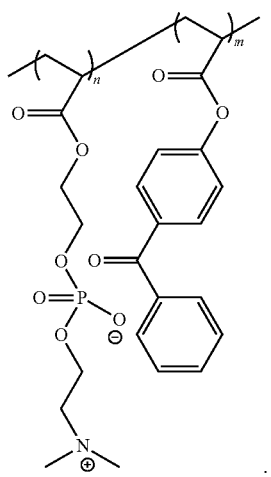

G

In some embodiments, the macroinitiator comprises at least one photosensitizer unit, which is included in the copolymerization with the hydrophilic monomer. The photosensitizer unit can be any photoinitiating monomer with any acrylated, methacrylated, or ethylenically unsaturated groups. Generally, any photoinitiating molecule with free hydroxyl or amino groups can be used to synthesize the photoinitiating monomer. Examples include, but are not limited to, 4-hydroxybenzophenone, 2-hydroxybenzophenone, 3-hydroxybenzophenone, 4,4'-dihydroxybenzophenone, 4'-hydroxyacetophenone, 2'-hydroxyacetophenone, 3'-hydroxyacetophenone, benzoin, 4,4'-dimethoxybenzoin, 1-hydroxycyclohexyl phenyl ketone, 2-hydroxy-2-methylpropiophenone, 4'-aminoacetophenone, 2-hydroxyacetophenone, 3'-aminoacetophenone, 4'-hydroxypropiophenone, 2-hydroxy-2-methylpropiophenone, 2'-aminoacetophenone, 4-aminobenzophenone, 2-bromo-4'-hydroxyacetophenone, 4'-hydroxy-3'-methylacetophenone, 4'-hydroxy-2'-methylacetophenone, Eosin derivatives including but not limited to eosin Y, and other similar types of photoinitiating monomers.

The macroinitiator can be synthesized by any radical polymerization, such as traditional free radical polymerization, atom transfer radical polymerization and reversible addition-fragmentation chain-transfer polymerization, or by cationic or anionic polymerization. The duration of the reaction time can be varied from 4 h to 50 h, for example, from 6 h to 40 h, from 8 h to 30 h, or from 10 h to 20 h. The temperature of the reaction can range from any temperature between 50 to 100° C., such as e.g., 55 to 90° C., 60 to 80° C. or 65 to 75° C. Examples of the solvents that can be used for the polymerization reaction include, but are not limited to, dimethylformamide, dimethyl sulfoxide, water, anisole, 1,4-dioxane, methanol, ethanol or the combination of more than one solvent.

The copolymerization of hydrophilic monomers and photoinitiating monomers can be initiated by any free radical initiator, including azo compounds, organic peroxides and inorganic peroxides, or redox initiating systems. In some embodiments, the initiator can be 2,2'-azobis(2-methylpropionitrile), 4,4'-azobis(4-cyanovaleric acid), 1,1'-azobis(cyclohexane-carbonitrile), 2,2'-azobis(2-methylpropionamidine) dihydrochloride, or any other similar azo compounds. In some embodiments, the initiator can be tert-butyl hydroperoxide, tert-butyl peracetate, cumene hydroperoxide, dicumyl peroxide, benzoyl peroxide, 2-butanone peroxide, tert-butyl peroxide, tert-butyl peroxybenzoate, ammonium persulfate, hydroxymethanesulfinic acid monosodium salt dehydrate, potassium persulfate, sodium persulfate, or any other organic or inorganic peroxide. In other embodiments, the initiator can be methyl α-bromoisobutyrate, ethyl α-bromoisobutyrate, 2-hydroxyethyl 2-bromoisobutyrate, tert-butyl α-bromoisobutyrate, or any other α-bromoisobutyrate compound able to initiate the radical polymerization reaction.

A polymer's hydrophilicity can be imparted by the chemical nature of the monomers comprising of the said polymer. In the case of the macroinitiator(s) as described herein, the polymer's hydrophilicity can be imparted by, for example, charged species, zwitterions, hydrogen bond donors, hydrogen bond acceptors, and/or other polar functional groups. Accordingly, in some embodiments, the polymer comprises a charged monomer containing either a positive or negative charge.

In some embodiments, the polymer comprises a monomer that is charged but yet has an overall neutral net charge, e.g., the monomer is zwitterionic. In some embodiments, the polymer comprises a monomer that is a betaine. It is known in the art that betaines are neutral chemical compound with a positively charged cationic functional group such as a quaternary ammonium or phosphonium cation, which bears no hydrogen atom and with a negatively charged functional group such as a carboxylate, sulfate, or phosphate group.

In other embodiments, the macroinitiator can be a randomized tri-polymer containing two different hydrophilic monomers and a photosensitizer unit. The macroinitiator can be a block tri-polymer or a tetra-polymer containing more than one different hydrophilic monomer and at least one or more different photosensitizer units. In a certain embodiment, the 50 k macroinitiator can be synthesized containing 6% (wt) 4-benzoylphenyl acrylate, 67.7% (wt) 2-hydroxyethyl acrylate, and 26.3% (wt) pyrrolidone.

Hydrophilic Polymers

The hydrophilicity and lubricity of the coating can be enhanced by addition of hydrophilic polymers. The macroinitiator can be dissolved in a compatible solvent in the presence of one or more hydrophilic polymer (FIG. 1) at a desired weight/volume (w/v) ratio. The hydrophilic polymer contributes to the hydrophilic and lubricious properties of the coating when in contact with water or an aqueous solution.

In some embodiments, the hydrophilic polymers are poly (vinylpyrrolidone) or any copolymers composed of monomeric units containing vinyl-pyrrolidone groups. Other examples of hydrophilic polymers include, but are not limited to, poly(acrylic acid), poly(methacrylic acid), poly (2-ethylacrylic acid), poly(2-propylacrylic acid), poly(sulfopropyl acrylate) potassium salt, poly(2-hydroxypropyl methacrylate), poly(2-methacryloyloxyethyl phosphorylchlorine), or any copolymers comprising of one or more of these groups. In some embodiments, the hydrophilic polymers are poly(vinyl alcohol), poly(ethylene glycol), or poly (ethylene oxide). In other embodiments, the hydrophilic polymers can be poly(2-oxazoline) and polyethylenimine, poly(N-isopropylacrylamide), or polyacrylamide. In certain embodiments, the hydrophilic polymers can be polyelectrolytes, such as poly(diallyldimethylammonium chloride), poly(vinylphosphonic acid), poly(vinyl sulfate) potassium salt, poly(vinylsulfonic acid, sodium salt), poly(styrenesulfonate), poly(allylamine hydrochloride), or any other similar water soluble polyelectrolyte. In other embodiments, the hydrophilic polymers can be polysaccharides, such as starches, glycogens, arabinoxylans, chitins, alginates, pectins, hyaluronic acid, acidic polysaccharides, or any other water soluble natural or synthetic polysaccharides.

Other examples of hydrophilic polymers include hydroxylated silicon oxide, polyethylene glycol, poloxamine, polysorbate, and polypropylene glycol, polyyrethane, isocyanate, polyethylene oxide, and other similar compounds.

In other embodiments, the hydrophilic polymers can range in molecular weight from 1 k to 2000 k, for example, from 2 k to 1000 k, from 3 k to 700 k, from 5 k to 500 k, from 7 k to 400 k, or from 10 k to 300 k.

In some embodiments, thermoplastic hydrophilic polymers comprise polyurethanes, polyether-amides block copolymers, polyethylene-acrylic acid copolymers, polyethylene oxide copolymers, ethylene acrylic esters copolymers, polylactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof.

In other embodiments, the hydrophilic polymer can be cross-linked by copolymerizing a hydrophilic monomer or linear polymer with a cross-linking agent, such as ethylene glycol diamethacrylate, or any hydrophilic monomers or polymers with a plurality of acrylate groups, in an aqueous solution. Cross-linked hydrophilic polymers can result in an interpenetrating network, which can interlock with the macroinitiator as it undergoes the free radical polymerization reaction on the latex surface. In a certain embodiment, lightly cross-linked pMPC is prepared by incubating of MPC monomer (5% w/v), ethylene glycol dimethacrylate (1% mol/mol of MPC), ammonium persulfate (0.005% w/v), and tetramethylethylenediamine (0.1% v/v) in water for 24 hours at room temperature.

Solution Preparation and Coating Application

In some embodiments, the macroinitiator and hydrophilic polymer are dissolved in a solvent that is compatible to the solubility of both components. Solvents can include, but are not limited to, water, ethanol, methanol, acetone, chloroform, acetonitrile, 2-propoanol, toluene, tetrahydrofuran, dimethylformamide, and dimethyl sulfoxide. The solvents used to prepare the solution must also be compatible to latex in a manner that will minimize degradation or damage inflicted to the material. In one embodiment, a mixture of ethanol and water can be used at ratios 10:1, 5:1, 5:2, 5:3, 5:4, 2:1, 1:1, 1:2, 4:5, 3:5, 2:5, 1:5, and 1:10 (part ethanol: part water). In another embodiment, the amount of macroinitiator dissolved in solution can range from about 0.1% (w/v) to about 20% (w/v) while the amount of the hydrophilic polymer dissolved solution can range from about 0.01% (w/v) to about 10% (w/v).

The amount of the hydrophilic polymer added in solution can affect the viscosity of the solution. Thus, the solution comprising the polymer can be viscous or non-viscous. As used herein, the term "viscous" means a liquid material, e.g., a solution comprising the polymer, with viscosity of several hundred centipoises to several million centipoises. For example the measurement of viscosity can range from about $10^2$ cP to about $10^6$ cP. In some embodiments, thickening agents can be introduced to increase the viscosity of the solution if desired to better tailor the coating application protocol or light-curing process when treating particular latex materials or natural rubber devices. Examples of thickening agents include, but are not limited to, celluloses, polyethylene glycol, polyethylene oxide, naturally occurring gums, gelatin, karaya, pectin, alginic acid, and povidone. Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carragenans, hyaluronates, and alginates. Additionally, this hydrophilic coating can be impregnated with pharmaceutical compounds and medications including, but not limited to anti-retroviral, antimicrobial, and antifungal medication.

Application of coating deposition onto latex or natural rubber materials or devices can include, but are not limited to, electrochemical deposition, deposition from an aerosolized spray, dispersion of polymers onto substrate for coating, solvent evaporation method, spontaneous emulsification, and electrochemical plating and/or deposition, or other similar processes.

A free radical photopolymerization reaction is performed to induce the covalent attachment of the macroinitiator on natural rubber that is composed of flexible chains of cis 1,4-polyisoprene, which are unsaturated carbon double bonds. The polymerization reaction is initiated when the photoinitiating units of the macroinitiator are exposed to a light source. Without wishing to be bound by theory, this absorption of energy can excite the photoinitiator units, allowing them to abstract hydrogen from the unsaturated carbon double bonds from the latex, or isoprene, surface. This leads to the generation of free radicals, which can ubiquitously initiate the covalent attachment of the macroinitiator to latex. As the macroinitiator covalently bonds to the natural rubber, the hydrophilic polymer becomes interpenetrated and entangled to the latex.

Photoinitiated polymerizations, photoinitiators, and methods of efficient UV-curing techniques are discussed in detail in "Radiation Curing in Polymer Science and Technology" volumes. I-IV eds. J. P. Fouassier and J. F. Rabek, London: Elsevier (1993); "Mechanisms of Photophysical Processes and Photochemical Reaction in Polymers" J. F. Rabek, New York: Wiley & Sons (1987); "Photoinitiation, Photopolymerization, and Photocuring" J. P. Fouassier, Cincinnati: Hanser Gardner (1995); Fisher et al. 2001, Ann. Rev. Mater. Res., 31:171.

To initiate the photopolymerization reaction, light can be applied for a period of a few seconds to several minutes or hours. In some embodiments, light can be applied for about 0.5 minutes to about 1 minute. In other embodiments, light can be applied for about 1 minute to about 30 minutes. In one embodiment, light exposure can be from about 3 minutes to about 10 minutes.

In some embodiments, free radicals from the macroinitiator can be initiated using a light source. The light source can emit light radially or non-radially. Useful light sources include, but are not limited to, lamps, fiber optics devices, and lasers. In one embodiment, the light source is a lamp. The light source can allow variation of the wavelength of light and/or the intensity of the light. For example, the reaction can be initiated using by UV light (200-500 nm). In other embodiments, long UV rays can be used. In other embodiments, short UV rays can be used. In some embodiments, the reaction can be initiated using visible light (400-800 nm). In other embodiments, the reaction can be initiated using blue light (420-500 nm). In other embodiments, the reaction can be initiated using green light (500-575 nm). In some embodiments, the reaction can be initiated using IR light (800-2500 nm). The output of light can be controlled to provide greater control over the reaction. In one embodiment, the reaction can be initiated using long UV rays at 365 nm.

In certain embodiments, the intensity of light ranges from about 500 to about 10,000 $\mu W/cm^2$. In some embodiments, the intensity of light is about 1000, about 2000, about 3000, about 4000, about 5000, or about 600 $\mu W/cm^2$. In one embodiment, the intensity of light is about 3000 $\mu W/cm^2$.

When a light source is used for the initiation of the photopolymerization, the polymerizable composition can further comprise one or a combination of two or more photoinitiators. In some embodiments, the photo-initiator can be a peroxide (e.g., ROOR'), a ketone (e.g., RCOR'), an azo compound (e.g., compounds with a —N=N— group), an acylphosphineoxide, a sulfur-containing compound, a quinone. Exemplary photo-initiators include, but are not limited to, acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenyl-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diefhylamino)benzophenone; 4,4'-bis(dimethylamino)benzophenone; Michler's ketone; camphorquinone; 2-chlorothioxanthen-9-one; 5-dibenzosuberenone; (cumene) cyclopentadienyliron(II) hexafluorophosphate; dibenzosuberenone; 2,2-diethoxyacetophenone; 4,4'-dihydroxybenzophenone; 2,2-dimethoxy2-phenylacetophenone; 4-(dimethylamino)benzophenone; 4,4'-dimethylbenzyl; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinoprpiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 2959 (CIBA Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl) propan 1-one; 1-hydroxy-cyclohexyl-phenyl-ketone; 2,4,6trimethylbenzoyldiphenylphosphine oxide; diphenyl(2,4,6trimethylbenzoyl)phosphine; 2-ethylhexyl-4 dimethylaminobenzoate; 2-hydroxy-2-methyl-1-phenyl-1 propanone; 65% (oligo[2-hydroxy-2-methyl-1-[4-(methylvinyl)phenyl]propanone] and 35% propoxylated glyceryl triacrylate; benzil dimethyl ketal; benzophenone; blend of benzophenone and α-hydroxy-cyclohexyl-phenylketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional α-hydroxy ketone; ethyl 4-(dimethylamino)benzoate; isopropyl thioxanthone; 2-hydroxy-2methyl-phenylpropanone; 2,4,6,-trimethylbenzoyldipheny 1 phosphine oxide; 2,4,6-trimethyl benzophenone; liquid blend of 4-methylbenzophenone and benzophenone; oligo (2-hydroxy-2 methyl-1-(4(1-methylvinyl)phenyl)propanone; oligo(2-hydroxy-2-methyl-1-4(1-methylvinyl)phenyl propanone and 2-hydroxy-2-methyl-1-phenyl-1-propanone (monomeric); oligo(2-hydroxy-2-methyl-1-4(1-methylvinyl)phenyl propanone and 2-hydroxy-2-methyl-1-phenyl-1propanone (polymeric); 4-methylbenzophenone; trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photo-initiator is acetophenone; diphenyl(2,4,6-trimethylbenzoyl)phosphine oxide; 4,4'-dimethoxybenzoin; anthraquinone; anthraquinone-2-sulfonic acid; benzene-chromium(O) tricarbonyl; 4-(boc-aminomethyl)phenyl isothiocyanate; benzil; benzoin; benzoin ethyl ether; benzoin isobutyl ether; benzoin methyl ether; benzophenone; benzoic acid; benzophenone/1 hydroxycyclohexyl phenyl ketone, 50/50 blend; benzophenone-3,3',4,4'-tetracarboxylic dianhydride; 4-benzoylbiphenyl; 2-benzyl-2-(dimethyl amino)-4' morpholinobutyrophenone; 4,4'-bis(diethylamino) benzophenone; Michler's ketone; (+)-camphorquinone; 2-chlorothioxanthen-9-one; 5-dibenzosuberenone; 2,2-diethoxyacetophenone; 4,4'-dihydroxybenzophenone; 2,2dimethoxy-2-phenylacetophenone; 4-(dimethylamino)benzophenone; 4,4'-dimethylbenzil; 3,4dimethylbenzophenone; diphenyl (2,4,6-trimethylbenzoyl) phosphine oxide/2-hydroxy methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methyl benzoylformate; 2-methyl-4'-(methylthio)-2-morpholinopropiophenone; 9, 10-phenanthrenequinone; 4'-phenoxyacetophenone; thioxanthen-9-one; triarylsulfonium hexafluorophosphate salts; 3-mercapto-1-propanol; 11-mercapto-1-undecanol; 1-mercapto-2-propanol; and 3-mercapto-2-butanol, all of which are commercially available from Sigma-Aldrich. In some embodiments, the free radical initiator is selected from the group consisting of benzophenone, benzyl dimethyl ketal, 2-hydroxy-2-methyl-phenylpropanone; 2,4,6-trimethylbenzoyldiphenyl phosphine oxide; 2,4,6-trimethyl benzophenone; oligo(2-hydroxy-2-methyl-1 (4-(1-methylvinyl)phenyl)propanone and 4-methylbenzophenone. In some embodiments, the photo-initiator is dimethoxy-2-phenyl-acetophenone (DMPA), a titanocene, 2-hydroxy-1-(4(hydroxyethoxy)phenyl)-2-methyl-1-propanone, Igracure. In some embodiments, the initiator is 2-hydroxy-1-(4-(hydroxyethoxy) phenyl)-2-methyl-1-propanone (Irgacure 2959, CIBA Chemicals).

In general, photoinitiators are utilized at concentrations ranging between approximately 0.005% (w/v) and 5.0% (w/v). For example, photo-initiators can be utilized at concentrations of about 0.005% (w/v), about 0.01% (w/v), about 0.025% (w/v), about 0.05% (w/v), about 0.075% (w/v), about 0.1% (w/v), about 0.125% (w/v), about 0.25% (w/v), about 0.5% (w/v), about 0.75% (w/v), about 1% (w/v), about 1.125% (w/v), about 1.25% (w/v), about 1.5% (w/v), about 1.75% (w/v), about 2% (w/v), about 2.125% (w/v), about 2.25% (w/v), about 2.5% (w/v), about 2.75% (w/v), about 3% (w/v), about 3.125% (w/v), about 3.25% (w/v), about 3.5% (w/v), about 3.75% (w/v), about 4% (w/v), about 4.125% (w/v), about 4.25% (w/v), about 4.5% (w/v), about 4.75% (w/v), about 5% (w/v) or higher, although high concentrations of photo-initiators may induce cytotoxicity.

In certain embodiments, chemical modifications and techniques, such as radical polymerizations, ionic polymerizations, photochemical initiation, thermal initiation, redox reaction, argon plasma treatment, and vapor phase plasma treatment, can be investigated to modify the chemical and physical properties of natural rubber prior to the application of the hydrophilic coating. Additionally the chemical processes and methods to covalently bond the hydrophilic coating macroinitiator onto natural rubber can be altered and/or controlled by adjusting the reaction conditions. For example, greater intensity of light, longer wavelengths or prolonged exposure will affect the amount of free radicals generated to promote the covalent bonding of the macroinitiator and hydrophilic polymer onto natural rubber. However intense or prolonged exposure to a certain light source may damage the integrity of latex. Therefore it is important to optimize these conditions to allow for covalent attachment of the hydrophilic coating while preventing or minimizing any causing any damage or adverse effects to natural rubber. One of ordinary skill in the art would be able to perform such an optimization of conditions using methods known in the art.

Once the coating is applied to the latex and exposed to a light source to induce the covalent attachment of the macroinitiator to the material, any unreacted or excessive macroinitiator or hydrophilic polymers can be removed by e.g., washing. The coated latex samples can be washed in a solvent or a mixture of solvents compatible to the solubility of the macroinitiator and hydrophilic polymer. The solvents used for the washing should also be compatible with latex without inducing degradation or damage to the material. In some embodiments, solvents for the washes can include, but are not limited to, water, ethanol, methanol, acetone, chloroform, acetonitrile, 2-propoanol, toluene, or mixtures of these solvents. In a preferred embodiment, a mixture of ethanol and water can be used at ratios 10:1, 5:1, 5:2, 5:3, 5:4, 2:1, 1:1, 1:2, 4:5, 3:5, 2:5, 1:5, and 1:10 part ethanol to part water. In some embodiments, the coated latex sample is washed by immersing the sample into a solvent for a desired period of time. In another embodiment, the washing can be performed by pouring solvent or a mixture of solvents over the coated surface of the latex sample for a certain period of time. In one embodiment, the coated latex samples are immersed in water for 10 minutes and then immersed in ethanol for another 10 minutes to perform the washes. In another embodiment, the coated latex samples are immersed in a mixture of water and ethanol (1:1 part) for 10 minutes with a stir bar to wash any excess or unreacted macroinitiator or hydrophilic polymers after light exposure.

Once the hydrophilic coating is applied onto the latex, exposed to a light source, and washed with solvents, any residual solvent should be removed before the hydrophilic coating can be characterized and assessed on the latex material. Solvent removal can be performed via evaporation, which can be assisted or expedited with heat, vacuum, or airflow. If solvent evaporation is performed in the presence of heat, heat exposure should be kept to a minimum to prevent damage inflicted to the latex material or degradation of the macroinitiators or polymers. In one embodiment, the coated latex samples are placed in an oven at 80° C. for 5 minutes after the washes are performed to evaporate any excess solvent. In another embodiment the coated latex samples are placed in a hood under a light air flow overnight for the solvent to evaporate.

In one embodiment, latex is washed with water and ethanol before it is prepared and mounted onto a glass slide. The homogeneous solution, consisting of the dissolved macroinitiator and hydrophilic polymer at desired concentrations, is applied evenly to cover the latex surface using a glass pipette. The sample is then immediately exposed to UV light to initiate the production of free radicals from the macroinitiator, which leads to the covalent attachment of the macroinitiator as well as the interpenetration and entanglement of the hydrophilic polymer onto the latex.

In another embodiment, a solution containing the macroinitiator and hydrophilic polymer at desired concentrations is prepared so that the latex or natural rubber surface can be covered using a dip-coating approach. The latex substrate is immersed in the solution for a desired duration and raised at a determined rate to ensure an even coating of the solution onto the latex. The sample is then immediately exposed to a light source, which results in a stable hydrophilic coating on the latex.

In some embodiments, the polymers, compositions and methods disclosed herein can be applied onto the latex surface several times to develop multilayered coatings by repeating the application protocol as desired. In a certain embodiment, the application, exposure, wash, and solvent evaporation are performed twice to produce a two-layered surface coating. In another embodiment, the application, exposure, wash, and solvent evaporation are repeated three times to produce a three-layered surface coating. The sequential coating process may be repeated a plurality of times.

In other embodiments, the macroinitiator and coating application protocol disclosed herein can be applied to other types of materials or devices made from latex or natural rubber, or other ethlenically unsaturated materials including, but not limited to, gloves, rubber bands, shoes, boots, clothing, kitchen appliances, and swimming wear.

In certain embodiments, the macroinitiator and hydrophilic coating application protocol can be used in a similar manner to treat other types of materials or devices developed from synthetically-made latex, as styrene-butadiene rubber, acrylonitrile butadiene rubber, acrylic polymers, polyvinyl acetate, or other types of materials containing ethylenically unsaturated groups.

In some embodiments, devices or materials can be pretreated or covered with a base layer or coating to make the surface compatible for the application of the hydrophilic coating using the macroinitiator using a light source as described herein. Examples include, but are not limited to devices and applications made from metal, wood, glass, silicone, polyurethane, and plastics.

Latex Articles

Essentially any latex article can be coated using the methods and macroinitiator compositions described herein. Exemplary latex articles are briefly described herein.

Latex or Rubber Condoms:

In a study examining condom breakage, a single predominant mechanism of failure was identified when the tip of the male penis progressively stretches one part of the intact condom wall until it ultimately breaks due to high frictional and shearing stress forces inflicted onto the latex material. This mechanism of failure is responsible for more than 90% of condom breakage and is not attributable to misuse.

Lubricants are introduced to minimize mechanical and frictional stresses inflicted onto the latex condom surface and tissue interface to prevent condom breakage and to protect mucosal barriers from microtrauma while also increasing pleasure between partners during intercourse. Although condoms packaged with lubrication are commercially available, pre-lubricated condoms fail to provide sufficient lubrication throughout intercourse and can wear off after a short period of time. Therefore external lubrication must be applied to maintain the condom's lubricity and to minimize friction between the condom surface and tissue interface. However oil-based lubricants can weaken latex, limiting condoms to serve as prophylactic devices by preventing the exchange of bodily fluids between partners potentially putting users at risk for sexually transmitted infections (STIs). Although water- or silicone-based personal lubricants can avoid degradative activity upon latex, these types of lubricants can easily slough off from the sliding interface between the condom surface and tissue interface over repetitive cyclically articulations, such as that experienced during sexual intercourse.

In one embodiment, the hydrophilic coating can be applied to latex-based prophylactic devices, such as latex condoms, to reduce friction and shearing forces experienced at the surface of the condom over a longer time period compared to other commercially available lubricants or personal massaging oils. This can result in decreased rates of condom breakage and a decreased degree of mucosal microtrauma associated with condom usage during penetration or sexual intercourse. The application of the hydrophilic coating to the condom surface can result in (i) a reduction in friction, (ii) decreased blunt microtrauma and potential tear to the condom, and (iii) decreased friability of the host mucosal membranes which may ultimately lead to lower rates of condom breakage, (iv) decreased rates of sexually transmitted infections (STIs), or (v) combinations thereof. In one embodiment, the thickness of the polymeric coating can be fabricated in the range of 1 nm to 100 μm to maintain a slim condom design. In another embodiment, the hydrophilic coating on the latex condom can reduce rates of the transmission of additional sexually transmitted infections (STIs) such as human immunodeficiency virus (HIV) herpes simplex and human papilloma virus (HPV) by providing an additional barrier.

The present disclosure of the macroinitiator and hydrophilic coating application also includes, but is not limited to, other types of prophylactic devices, such as male and female contraceptive latex-based devices. In one embodiment, the hydrophilic coating of the present invention can be applied onto other types of sexual stimulation devices including but not limited to penile-replicative devices, vaginal-replicated devices, anal-replicated devices, oral-replicated devices, and other similar devices commonly referred to as "sex toys," medical catheters including urinary and intravascular catheters, prosthetic devices, endoscopic and laparoscopic devices, electromedicine devices, and medical probes such as transvaginal (e.g., transvaginal ultrasound probes) and transrectal probes.

Incorporation of Bioactive Agents in Polymer

In certain embodiments, the hydrophilic coating and solution preparation comprising the macroinitiator and hydrophilic polymer can also include antimicrobials such as antibacterials, antiretrovirals, antivirals, antifungals, and metallic nanoparticles and/or microparticles focused on deterring microbial growth. Examples of suitable antifungal agents include lactic acid, sorbic acid, Amphotericin B, Ciclopirox, Clotrimazole, Enilconazole, Econazole, Fluconazole, Griseofulvin, Halogropin, Introconazole, Ketoconazole, Miconazole, Naftifine, Nystatin, Oxiconazole, Sulconazole, Thiabendazole, Terbinafine, Tolnaftate, Undecylenic acid, Mafenide, Silver Sulfadiazine, and Carbol-Fushsin. Additionally, antibiotics and other antimicrobial agents can be selected from the group consisting of bacitracin; the cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, the penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; the polymyxins (such as colistin, colistimathate, and polymyxin B); the aminoglycosides (such as amikacin, gentamicin, kanamycin, neomycin, netilmicin, paromomycin, spectinomycin, streptomycin, and tobramycin), the tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin; other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim. Other antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; and benzoic acid.

A therapeutically effective amount is an amount of an agent that is sufficient to produce a statistically significant, measurable change in at least one symptom of the disease to be treated. Such effective amounts can be gauged in clinical trials as well as animal studies for a given agent.

In some embodiments, the bioactive agent will be released from the polymer, for example, over time as in a drug-eluting implant. In other embodiments, the bioactive agent will be retained in the polymer for use as a localized treatment (e.g., treatment or prevention of sexually transmitted infections by use of a medicated condom). The dosage range for the bioactive agent depends upon the potency, and includes amounts large enough to produce the desired effect, e.g., treatment or prevention of infection, such as a sexually transmitted disease. The dosage should not be so large as to cause unacceptable adverse side effects. Generally, the dosage will vary with the type of bioactive (e.g., an antibody, small molecule, siRNA, etc.) and with the age, condition, and sex of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

In some embodiments, the coated latex article used to administer the bioactive agent provides sustained delivery, such as "slow release" of the active compound to a subject. For example, the latex article can deliver the agent or composition for at least one, two, three, or four weeks after the latex article is implanted or otherwise administered to the subject. Preferably, a subject to be treated in accordance with the methods described herein is treated with the active composition for at least 30 days (either by repeated administration or by use of a sustained delivery system, or both).

As used herein, the term "sustained delivery" is intended to include continual delivery of the bioactive agent in vivo over a period of time following administration, preferably at least several days, a week, several weeks, one month or longer. Sustained delivery of the bioactive compound can be demonstrated by, for example, the continued therapeutic effect of the composition over time (such as sustained delivery of the agents can be demonstrated by continued improvement or maintained improvement of a disease in a subject). Latex articles, as described herein, can be drug-delivery devices that provide sustained delivery, such as e.g., a polymeric capsule, a minipump, or a biodegradable implant.

Therapeutic compositions containing at least one bioactive agent can be conventionally administered in a unit dose. The term "unit dose" when used in reference to a bioactive agent refers to physically discrete units suitable as unitary dosage for the subject, each unit containing a predetermined quantity of active material calculated to produce the desired therapeutic effect in association with the required physiologically acceptable diluent, i.e., carrier, or vehicle.

The efficacy of a given treatment for treatment of a disease (e.g., an STD) as described herein can be determined by the skilled clinician. However, a treatment is considered "effective treatment," as the term is used herein, if any one or all of the signs or symptoms of the disease is/are altered in a beneficial manner (e.g., reduction or amelioration of bacteria etc.), other clinically accepted symptoms or markers of disease are improved, or even ameliorated, e.g., by at least 10% following treatment with a bioactive agent. Efficacy can also be measured by failure of an individual to worsen as assessed by stabilization of the disease, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of a disease; or (2) relieving the disease, e.g., causing regression of symptoms; and (3) preventing or reducing the likelihood of the development of a disease.

The present invention may be as defined in any one of the following numbered paragraphs:

1. A composition comprising: a latex article having at least one layer of a hydrophilic coating, wherein the hydrophilic coating comprises a macroinitiating co-polymer and a hydrophilic polymer that form an interpenetrating co-polymer network on the surface of the latex article.

2. The composition of paragraph 1, wherein the latex article is selected from the group consisting of male condoms, female condoms, latex-based gloves, biomedical devices, sexual stimulation devices, contact lenses, rubber bands, shoes, clothing, kitchen appliances, swimwear, sportswear, sporting instruments, boats, vehicles, military devices, or toys.

3. The composition of paragraph 1 or 2, wherein the biomedical device comprises drug delivery devices, in vivo or in vitro diagnostic devices, medical catheters, balloons, stents, grafts, endoscopic devices, laparoscopic devices, electromedicine devices, or medical implants.

4. The composition of paragraph 1, 2, or 3, wherein the macroinitiating co-polymer is covalently linked to the latex article and the hydrophilic polymer is entangled within the macroinitiating co-polymer.

5. The composition of any one of paragraphs 1-4, wherein the macroinitiating co-polymer comprises a randomized co-polymer.

6. The composition of any one of paragraphs 1-5, wherein the macroinitiating co-polymer comprises one or more hydrophilic monomers that contain an acrylated, methacrylated, acrylamide, vinyl, or ethylenically unsaturated chemical group and a photosensitizer.

7. The composition of any one of paragraphs 1-6, wherein the macroinitiating co-polymer comprises a Formula selected from the group consisting of Formulas A-H Formulas A-H.

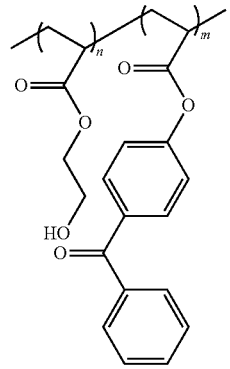

A

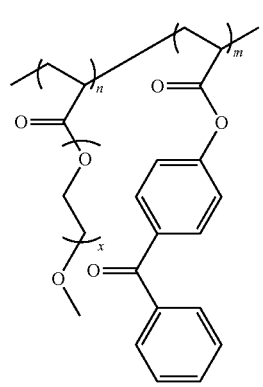

B

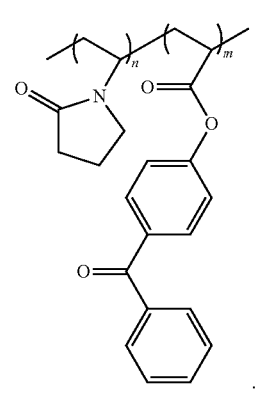

C

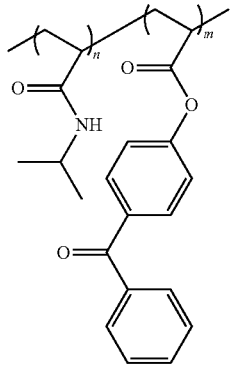

D

E
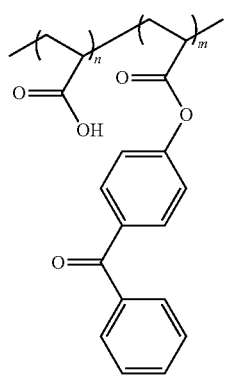

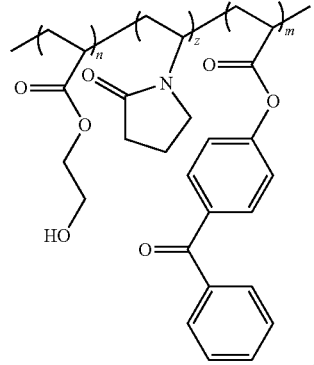

F

G
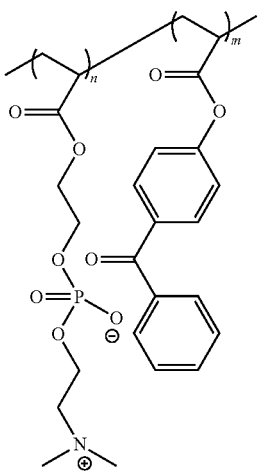

H wherein:
a) n and m are integers that represent the number of randomized repeat unit in which n can range from 10 to 5000 and m can range from 1% to 50% w/w of "n";
b) X is O or N—H;
c) $R_1$ and $R_2$ can be a hydrogen, methyl, ethyl, or propyl group;
d) $R_3$ and $R_4$ can be hydrogen, sodium, potassium, 2-hydroxyethyl, 3-hydroxypropyl, 4-hydroxybutyl, 2-carboxyethyl, 3-carboxypropyl, 4-carboxybutyl, polyethylene glycol, isopropyl, 2-(trimethylammonium)ethyl, 3-(trimethylammonium)propyl, 2-(phosphorylcholine)ethyl, 3-sulfopropyl potassium salt, 2-(N-3-sulfopropyl-N,N-dimethyl ammonium)ethyl, 3-(N-3-sulfopropyl-N,N-dimethyl ammonium)propyl,
and combinations thereof.

8. The composition of paragraph 5, wherein the randomized co-polymer comprises: (i) 2-hydroxyethylacrylate and a benzophenone polymer (HEA/BP) or (ii) acrylic acid and a benzophenone polymer (AA/BP).

9. The composition of paragraph 2, wherein the macro-initiating polymer comprises a charged monomer, a zwitterionic monomer, a betaine monomer, or a carbohydrate or polysaccharide monomer.

10. The composition of any one of paragraphs 1-9, wherein the hydrophilic polymer is selected from the group consisting of

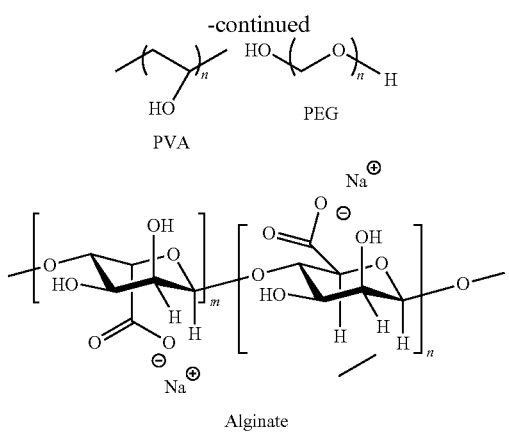

PVA

PEG

Alginate and combinations thereof.

11. The composition of any one of paragraphs 1-10, wherein the hydrophilic polymer is lightly cross-linked.

12. The composition of any one of paragraphs 1-11, wherein the hydrophilic polymer comprises a molecular weight in the range of 2 k to 10000 k.

13. The composition of any one of paragraphs 1-12, wherein the hydrophilic polymer comprises a thermoplastic polymer, a polysaccharide, or a charged hydrophilic polymer.

14. The composition of paragraph 10, wherein the hydrophilic polymer is selected from the group consisting of polyvinypyrrilidone, poly(2-methacryloyloxyethyl phosphorylchlorine), polyethylene oxide, or polyethylene glycol.

15. The composition of any one of paragraphs 1-14, further comprising at least one bioactive agent.

16. The composition of paragraph 15, wherein the bioactive agent comprises an antimicrobial agent, an antibacterial agent, an antiretroviral agent, an antiviral agent, an antifungal agent, an anti-neoplastic/tumor agent, an anticoagulant, an antiplatelet agent, a thromboplastic agent, an anti-growth agent, a metallic nanoparticle, a growth agent, genetic or viral materials, a hormonal agent, a radioactive agent, a diagnostic imaging agent, a biosensor, or pharmaceutical formulations or combinations thereof.

17. The composition of any one of paragraphs 1-16, wherein the hydrophilic coating is evenly distributed over the area of the latex article.

18. A method for coating a latex article with a hydrophilic coating, the method comprising: (a) contacting a latex article with a macroinitiating co-polymer and a hydrophilic polymer, (b) exposing the latex article to a light source, thereby coating the latex article with a hydrophilic coating.

19. The method of paragraph 18, wherein the latex article is selected from the group consisting of male condoms, female condoms, latex-based gloves, biomedical devices, sexual stimulation devices, contact lenses, rubber bands, shoes, clothing, kitchen appliances, swimwear, sportswear, sporting instruments, boats, vehicles, military devices, or toys.

20. The method of paragraph 19, wherein the biomedical device comprises drug delivery devices, in vivo or in vitro diagnostic devices, medical catheters, balloons, stents, grafts, endoscopic devices, laparoscopic devices, electromedicine devices, or medical implants.

21. The method of paragraph 18, 19, or 20, wherein the macroinitiating co-polymer is covalently linked to the latex article and the hydrophilic polymer is entangled within the macroinitiating co-polymer.

22. The method of any one of paragraphs 18-21, wherein the macroinitiating co-polymer comprises a randomized co-polymer.

23. The method of any one of paragraphs 18-22, wherein the macroinitiating co-polymer comprises one or more hydrophilic monomers that contain an acrylated, methacrylated, acrylamide, vinyl, or ethylenically unsaturated chemical group and a photosensitizer.

24. The method of any one of paragraphs 18-23, wherein the macroinitiating co-polymer comprises a Formula selected from the group consisting of Formulas A-H Formulas A-H.

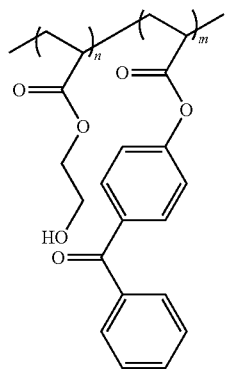

A

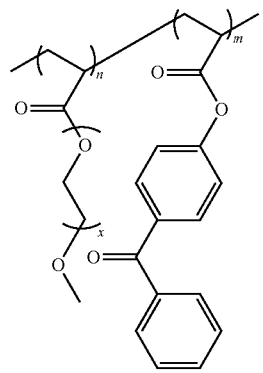

B

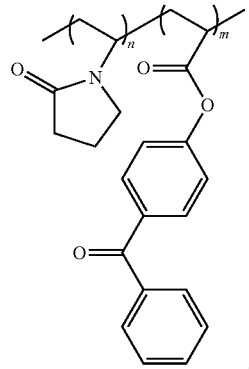

C

D

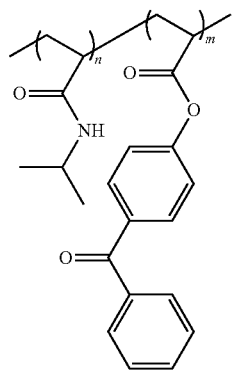

E

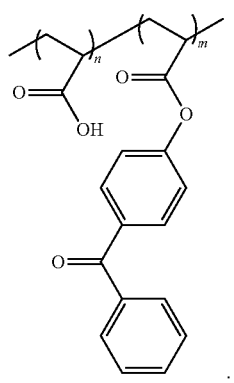

F

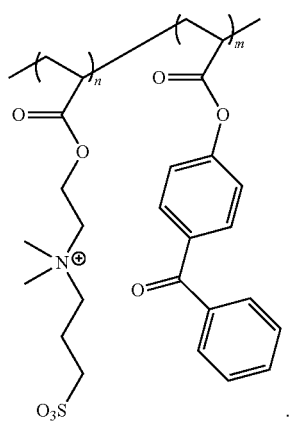

G

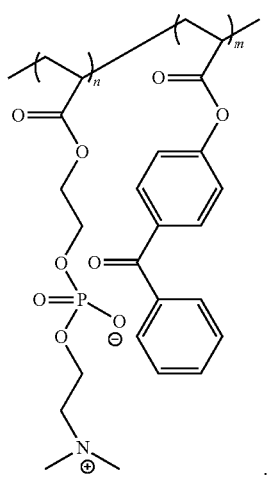

H

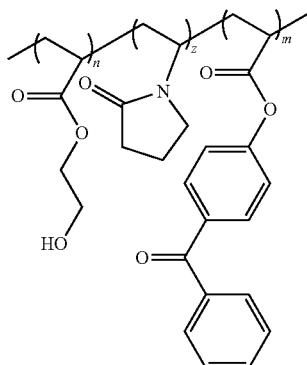

wherein:
a) n and m are integers that represent the number of randomized repeat unit in which n can range from 10 to 5000 and m can range from 1% to 50% w/w of "n";
b) X is O or N—H;
c) $R_1$ and $R_2$ can be a hydrogen, methyl, ethyl, or propyl group;
d) $R_3$ and $R_4$ can be hydrogen, sodium, potassium, 2-hydroxyethyl, 3-hydroxypropyl, 4-hydroxybutyl, 2-carboxyethyl, 3-carboxypropyl, 4-carboxybutyl, polyethylene glycol, isopropyl, 2-(trimethylammonium)ethyl, 3-(trimethylammonium)propyl, 2-(phosphorylcholine)ethyl, 3-sulfopropyl potassium salt, 2-(N-3-sulfopropyl-N,N-dimethyl ammonium)ethyl, 3-(N-3-sulfopropyl-N,N-dimethyl ammonium)propyl, and combinations thereof.

25. The method of paragraph 22, wherein the randomized co-polymer comprises: (i) 2-hydroxyethylacrylate and a benzophenone polymer (HEA/BP) or (ii) acrylic acid and a benzophenone polymer (AA/BP).

26. The method of any one of paragraphs 18-25, wherein the macroinitiating polymer comprises a charged monomer, a zwitterionic monomer, a betaine monomer, or a carbohydrate or polysaccharide monomer.

27. The method of any one of paragraphs 18-26, wherein the hydrophilic polymer is selected from the group consisting of

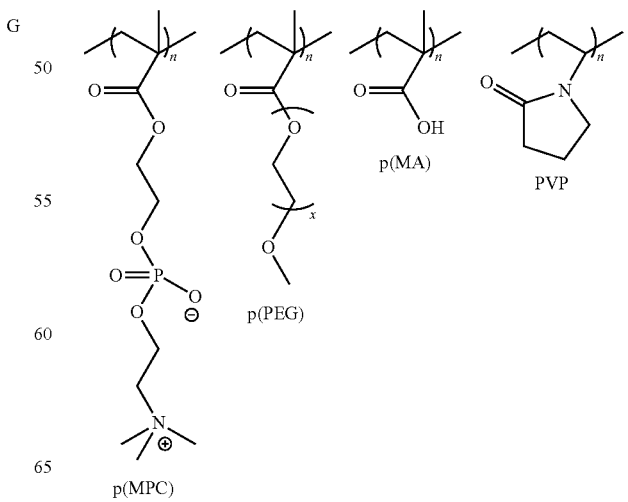

-continued

PVA

Alginate and combinations thereof.

28. The method of any one of paragraphs 18-27, wherein the hydrophilic polymer is lightly cross-linked.

29. The method of any one of paragraphs 18-28, wherein the hydrophilic polymer comprises a molecular weight in the range of 2 k to 10000 k.

30. The method of any one of paragraphs 18-29, wherein the hydrophilic polymer comprises a thermoplastic polymer, a polysaccharide, or a charged hydrophilic polymer.

31. The method of paragraph 27, wherein the hydrophilic polymer is selected from the group consisting of polyvinypyrrilidone, poly(2-methacryloyloxyethyl phosphorylchlorine), polyethylene oxide, or polyethylene glycol.

32. The method of any one of paragraphs 18-31, further comprising a bioactive agent.

33. The method of paragraph 32, wherein the bioactive agent comprises an antimicrobial agent, an antibacterial agent, an antiretroviral agent, an antiviral agent, an antifungal agent, an anti-neoplastic/tumor agent, an anticoagulant, an antiplatelet agent, a thromboplastic agent, an anti-growth agent, a metallic nanoparticle, a growth agent, genetic or viral materials, a hormonal agent, a radioactive agent, a diagnostic imaging agent, a biosensor, or pharmaceutical formulations or combinations thereof.

34. The method of any one of paragraphs 18-33, wherein the hydrophilic coating is evenly distributed over the area of the latex article.

35. The method of any one of paragraphs 18-34, wherein the macroinitiating polymer is synthesized via a polymerization reaction.

36. The method of paragraph 35, wherein the polymerization reaction is initiated by a free radical initiator selected from the group consisting of an azo compound, an organic peroxide, an inorganic peroxide, and a redox initiating system.

37. The method of paragraph 35, wherein the polymerization reaction is initiated by a traditional free radical reaction, atom transfer radical polymerization, reversible addition-fragmentation chain transfer polymerization, cationic or anionic polymerization or a light source.

38. The method of paragraph 37, wherein the light source is selected from the group consisting of a lamp, a fiber optic device, a UV source, and a laser.

39. The method of paragraph 35, wherein the reaction time of the polymerization reaction is from 4 hr to 50 hr.

40. The method of paragraph 35, wherein the polymerization reaction is performed at a temperature between 75-100° C.

41. The method of any one of paragraphs 18-40, wherein the macroinitiating polymer is dissolved in one or more solvents.

42. The method of paragraph 28, wherein the hydrophilic polymer is lightly crosslinked by contacting the hydrophilic monomers with a cross-linking agent.

43. The method of paragraph 42, wherein the cross-linking agent is ethylene glycol diamethacrylate.

44. The method of any one of paragraphs 18-43, wherein the hydrophilic polymer is dissolved in solution at a range of 0.1% (w/v) to 10 (w/v) %.

45. The method of any one of paragraphs 18-44, further comprising a step of adding a thickening agent.

46. The method of any one of paragraphs 18-45, wherein the macroinitiating co-polymer and the hydrophilic polymer are applied to the latex article via electrochemical deposition, electrochemical plating, deposition from an aerosolized spray, a solvent evaporation method, a dip-coating method or by using a pipette to apply a thin, even layer onto a natural or synthetic rubber surface manually.

47. The method of any one of paragraphs 18-46, wherein the macroinitiating copolymer and the hydrophilic polymer are applied to the latex article via a spraying method.

48. The method of any one of paragraphs 18-47, wherein the latex article is pre-treated using a chemical modification process.

49. The method of any one of paragraphs 18-48, wherein the chemical modification process comprises a radical polymerization, an ionic polymerization, a photochemical initiation, a thermal initiation, a redox reactions, an argon plasma treatment or a vapor phase plasma treatment.

50. The method of any one of paragraphs 18-49, further comprising a step of washing the coated latex article to remove excess macroinitiating co-polymer or hydrophilic polymer.

EXAMPLES

Example 1

Synthesis of 4-benzoylphenyl acrylate

To a round-bottom flask, 4-hydroxybenzophenone (20.0 g, 100 mol) and triethylamine (20.6 mL, 150 mol) were added and dissolved in 100 mL of anhydrous tetrahydrofuran. The reaction was equipped with a magnetic stirrer bar and cooled to 0° C. Acryloyl chloride (9.2 mL, 120 mol in 50 mL) was added dropwise to the mixture through an addition funnel. The reaction mixture was warmed to room temperature and stirred for 3 hours. The precipitate was isolated by filtration and the solvent was removed by rotary evaporation from the filtrate. The residue was dissolved in 100 mL ethyl acetate and the resultant solution was washed with 0.1M hydrochloric acid, saturated sodium bicarbonate solution, and saturated brine. The combined organic layers were dried over $Na_2SO_4$ and then concentrated in vacuum to afford a crude product. The crude product was purified by column chromatography (7:1 hexane:ethyl acetate) to yield 4-benzoylphenyl acrylate as a light yellow solid (24.8 g, yield=97.2%).

Example 2

Synthesis of the HEA/BP Macroinitiator with $MW_{THEO}$ of 50 k and 6% (w/w) BP to HEA To a round bottom flask, 2-hydroxyethyl acrylate (9.4 g, 82.5 mmol, distilled under vacuum before use), 4-benzoylphenyl acrylate (0.60 g, 2.4 mmol), and 2, 2'-azobis(2-methylpropionitrile) (16.4 mg, 0.10 mmol) were dissolved in dimethylformamide (30 mL), placed in a 100 mL Schlenk tube, and degassed via freeze-thaw cycles prior to the reaction. The reaction mixture was placed in an oil bath at 70° C. for 18 h. After the reaction, the polymers were dialyzed against distilled water using a 3 k molecular weight cut off (MWCO) dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 3

Synthesis of the HEA/BP Macroinitiator with $MW_{THEO}$ of 50 k and 10% (w/w) BP to HEA To a round bottom flask, 2-hydroxyethyl acrylate (9.0 g, 77.6 mmol, distilled under vacuum before use), 4-benzoylphenyl acrylate (1.0 g, 4.0 mmol), and 2, 2'-azobis(2-methylpropionitrile) (16.4 mg, 0.10 mmol) were dissolved in dimethylformamide (30 mL), placed in a 100 mL Schlenk tube, and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 4

Synthesis of the HEA/BP Macroinitiator with $MW_{THEO}$ of 150 k and 6% (w/w) BP to HEA To a round bottom flask, 2-hydroxyethyl acrylate (9.4 g, 82.5 mmol, distilled under vacuum before use), 4-benzoylphenyl acrylate (0.60 g, 2.4 mmol), and 2, 2'-azobis(2-methylpropionitrile) (5.3 mg, 0.033 mmol) were dissolved in dimethylformamide (30 mL), placed in a 100 mL Schlenk tube, and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 5

Synthesis of the AA/BP Macroinitiator with $MW_{THEO}$ of 50 k and 3% (w/w) BP to AA To a round bottom flask, acrylic acid (9.7 g, 134.7 mmol, distilled under vacuum before use), 4-benzoylphenyl acrylate (0.30 g, 1.2 mmol), and 2, 2'-azobis(2-methylpropionitrile) (16.4 mg, 0.10 mmol) were dissolved in dimethylformamide (30 mL), placed in a 100 mL Schlenk tube, and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 6

Synthesis of the AA/BP Macroinitiator with $MW_{THEO}$ of 50 k and 6% (w/w) BP to AA To a round bottom flask, acrylic acid (9.4 g, 130.5 mmol, distilled under vacuum before use), 4-benzoylphenyl acrylate (0.60 g, 2.4 mmol), and 2, 2'-azobis(2-methylpropionitrile) (16.4 mg, 0.10 mmol) were dissolved in dimethylformamide (30 mL), placed in a 100 mL Schlenk tube, and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 7

Synthesis of the AA/BP Macroinitiator with $MW_{THEO}$ of 50 k and 10% (w/w) BP to AA To a round bottom flask, acrylic acid (9.0 g, 130.5 mmol, distilled under vacuum before use), 4-benzoylphenyl acrylate (1.0 g, 4.0 mmol), and 2, 2'-azobis(2-methylpropionitrile) (16.4 mg, 0.10 mmol) were dissolved in dimethylformamide (30 mL), placed in a 100 mL Schlenk tube and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 8

Synthesis of the AA/BP Macroinitiator with $MW_{THEO}$ of 150 k and 6% (w/w) BP to AA To a round bottom flask, acrylic acid (9.4 g, 130.5 mmol, distilled under vacuum before use), 4-benzoylphenyl acrylate (0.60 g, 2.4 mmol), and 2, 2'-azobis(2-methylpropionitrile) (5.3 mg, 0.033 mmol) were dissolved in dimethylformamide (30 mL), placed in a 100 mL Schlenk tube and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via $^1$H NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 9

Sample Preparation, Hydrophilic Coating Application, IR Characterization, and Contact Angle Measurement of Coated Latex Sheets Using Macroinitiator HEA/BP (2% (w/v)) and PVP (2% (w/v))

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 2% (w/v) solution. Another solution was prepared in a similar manner containing the HEA/BP macroinitiator at 2% (w/v) and PVP (MW 360 k) at 2% (w/v). The solutions were mixed until homogeneous and evenly applied onto the surface of the latex using a glass pipet. The samples were immediately exposed to UV light (365 nm) for 15 or 30 minutes and then washed with water for 20 minutes and with ethanol for another 20 minutes to get rid of any excess or unreacted material from the coating. The samples were placed in an 80° C. oven for 5 minutes to evaporate the solvent. The lubricity and stability of the coating were tested by rubbing the latex coated samples for 30 seconds with distilled water. The presence of the coating was characterized with ATR-FTIR. Carbonyl peaks were observed in the 1731 cm$^{-1}$ and 1655 cm$^{-1}$ regions, which indicate the presence of HEA or PVP on the latex, respectively. The contact angles of the treated samples were measured and compared to non-coated latex samples to characterize the hydrophilicity of the coating. The contact angles of non-coated latex, coated latex with HEA/BP, and coated latex with HEA/BP and PVP were 117.2±5.6, 100.8±4.7, and 83.1±9.8, respectively, which indicated the presence of a more hydrophilic surface for the coated latex samples in comparison to the non-coated latex controls. All contact angle measurements were performed in triplicate.

Example 10

Sample Preparation, Hydrophilic Coating Application, and SEM Images of Coated Latex Sheets Using Macroinitiator HEA/BP (2% (w/v)) and PVP (2% (w/v))

Figure 2:
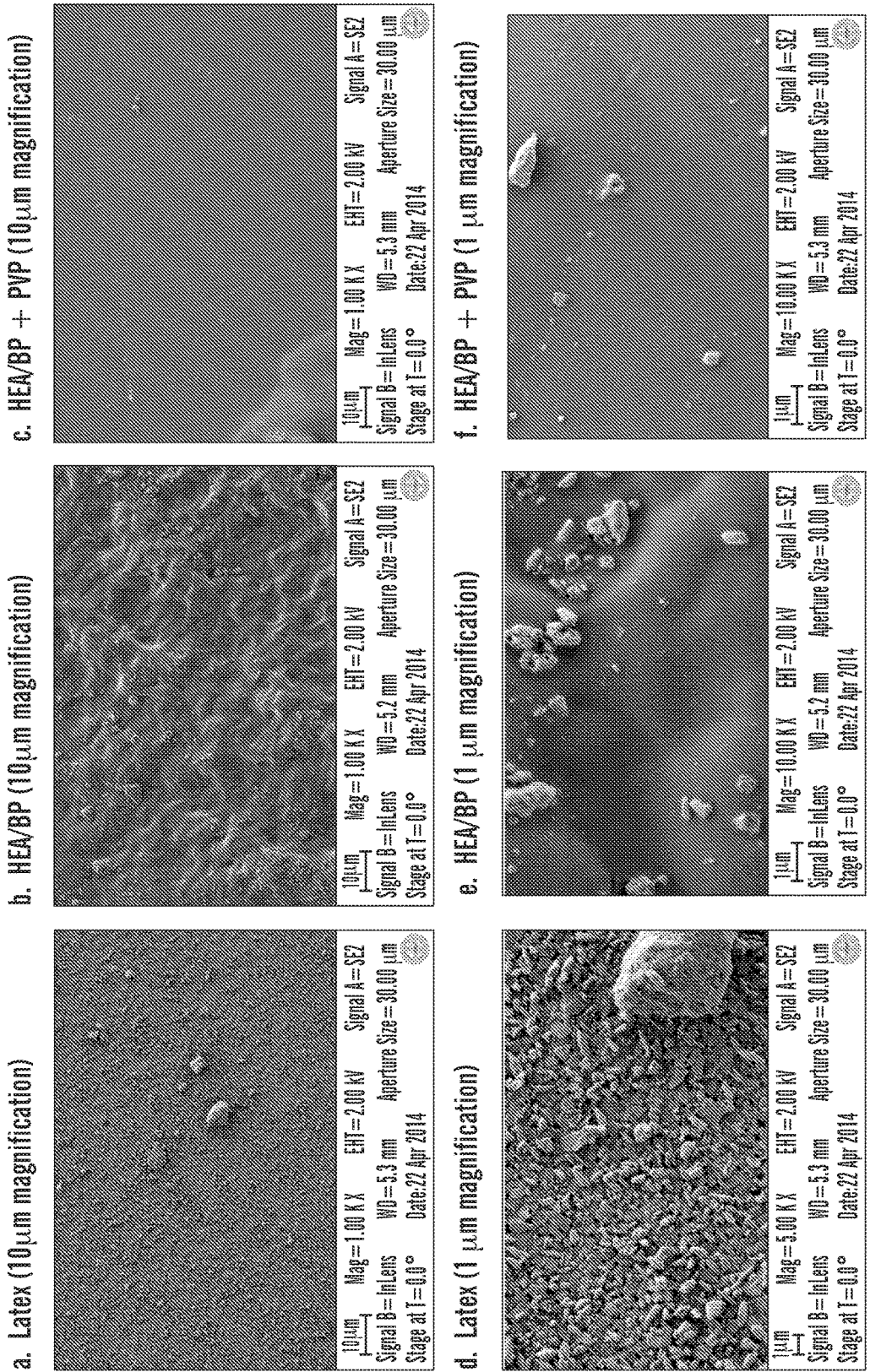
FIGS. 2A-2F show SEM images depicting latex samples with and without treatment of the hydrophilic coating at 1 μm or 10 μm magnification.

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 2% (w/v) solution. Another solution was prepared in a similar manner containing the HEA/BP macroinitiator 2% (w/v) and PVP (MW 360 k) 2% (w/v). The solutions were mixed until homogeneous and evenly applied onto the surface of the latex using a glass pipet. The samples were immediately exposed to UV light (365 nm) for 15 minutes and then washed with water for 20 minutes and with ethanol for another 20 minutes to get rid of any excess or unreacted material from the coating. The samples were placed in an 80° C. oven for 5 minutes to evaporate the solvent. The coated latex samples were carefully removed from the glass slide, cut into 1×1 cm sections, and mounted on SEM stubs covered in copper tape. SEM images were obtained at 10 μm and 1 μm magnification to observe the latex surface with and without the coatings (FIG. 2).

Example 11

Sample Preparation and Hydrophilic Coating Application Using Macroinitiator HEA/BP (5% (w/v)) and PVP (2% (w/v))

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 5% (w/v) solution. Another solution was prepared in a similar manner containing the HEA/BP macroinitiator 5% (w/v) and PVP (MW 360 k) 2% (w/v). The solutions were mixed until homogeneous and evenly applied onto the surface of the latex using a glass pipet. The samples were immediately exposed to UV light (365 nm) for 30 minutes and then washed with water for 20 minutes and with ethanol for another 20 minutes to get rid of any excess or unreacted material from the coating. The samples were placed in an 80° C. oven for 5 minutes to evaporate the solvent. The lubricity and stability of the coating were tested by rubbing the latex coated samples for 30 seconds with distilled water.

Example 12

Sample Preparation, Hydrophilic Coating Application Using Macroinitiator HEA/BP (5% (w/v)) and PVP (2% (w/v)), and Diffusion Testing to Detect Pores or Damage of Latex A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 5% (w/v) solution. Another solution was prepared in a similar manner containing the HEA/BP macroinitiator 5% (w/v) and PVP (MW 360 k) 2% (w/v). The solutions were mixed until homogeneous and evenly applied onto the surface of the latex using a glass pipet. The samples were immediately exposed to UV light (365 nm) for 30 minutes and then washed with water for 20 minutes and with ethanol for another 20 minutes to get rid of any excess or unreacted material from the coating. The samples were placed in an 80° C. oven for 5 minutes to evaporate the solvent. To determine whether the coating application, UV exposure, and heat exposure imposed any damage to the latex, a diffusion test was performed using an apparatus described in FIG. 3. Chamber 1 was filled with 40 mL of a fluorescein sodium salt 2.5% (w/v) solution in distilled water and chamber 2 was filled with 1 mL of distilled water. Latex samples, both coated and non-coated were placed between the two chambers at the connecting point to serve as a barrier between the two chambers. Stir bars were placed in both chambers and aliquots were taken from chamber 2 at varying time points up to 24 hours and refilled with distilled water. Fluorescence signal from the aliquots were measured at $\lambda_{ex}$=460 nm and $\lambda_{em}$=515 nm and compared to a standard curve of known fluorescein sodium salt concentrations to detect any presence of fluorescein sodium salt from chamber 1 diffusing into chamber 2 through the latex barrier. Fluorescein sodium salt was not detected in chamber 2 after 24 hours indicating that both non-coated and coated latex samples were be effective barriers and damage to the latex was not detected.

Example 13

Sample Preparation, Hydrophilic Coating Application, and Contact Angle Measurement of Coated Latex Sheets Using Macroinitiator AA/BP (2% (w/v)) and PVP (2% (w/v))

A sheet of latex was washed with water and ethanol, air-dried for 10 minutes, cut into 2×0.5 inch pieces, and mounted on glass slides. The AA/BP macroinitiator was dissolved in a water/ethanol solution (1:1 part) to prepare a 2% (w/v) solution. Another solution was prepared in a similar manner containing the AA/BP macroinitiator 2% (w/v) and PVP (MW 360 k) 2% (w/v). A small amount of 1 M sodium hydroxide was added to the solution sample containing the AA/BP macroinitiator and PVP to prevent hydrogen bonding and aggregation between the two linear polymers. The solutions were mixed until homogeneous, which resulted in a viscous solution, and evenly applied onto the surface of the latex using a glass pipet. The samples were immediately exposed to UV light (365 nm) for 10 minutes and then washed with water for 10 minutes and with ethanol for another 10 minutes to get rid of any excess or unreacted material from the coating. The samples were placed in an 80° C. oven for 5 minutes to evaporate the solvent. The lubricity and stability of the coating were tested by rubbing the latex coated samples for 30 seconds with distilled water. The contact angles of the treated samples were measured and compared to non-coated latex samples to characterize the hydrophilicity of the coating. The contact angles of non-coated latex, coated latex with AA/BP, and coated latex with AA/BP and PVP were 117.2±5.6, 87.1±2.8, and 32.8±8.8, respectively, which indicated the presence of a more hydrophilic surface for the coated latex samples in comparison to the non-coated latex controls. All contact angle measurements were performed in triplicate.

Example 14

Gel Permeation Chromatography (GPC) Characterization of the AA/BP Macroinitiator Samples of previously synthesized AA/BP macroinitiators, with a theoretical molecular weight of 50 k and 150 k, were dissolved in a buffered solution (0.1 M $NaNO_3$, 0.01 M $Na_2HPO_4$, 0.02 wt % $NaN_3$, pH 7.4, HPLC-grade water) at a 5 mg/mL concentration and filtered through a syringe filter with 0.22 μm pore size. The molecular weights of the two AA/BP macroinitiators were determined against poly (acrylic acid) standards. The results are listed in Table 1.

TABLE 1

| GPC characterization of the AA/BP macroinitiator against poly(acrylic acid) standards | | | | |
|---|---|---|---|---|
| $MW_{Theo}$ | $MW_{GPC}$ | $M_p$ | $M_n$ | PDI |
| 50 000 | 81 777 | 99 129 | 24 430 | 3.35 |
| 150 000 | 98 064 | 107 766 | 43 540 | 2.25 |

Example 15

Sample Preparation and Hydrophilic Coating Application of Coated Latex Sheets Using Macroinitiator HEA/BP (5% (w/v)) and pMPC (2% (w/v))

A sheet of latex was washed with water and ethanol, air-dried for 10 minutes, cut into 2×0.5 inch pieces, and mounted on glass slides. Lightly cross-linked pMPC was prepared prior to solution preparation by incubation of MPC (5 w/v %), ethylene glycol dimethacrylate (1 mol/mol % of MPC), ammonium persulfate (0.005 w/v %), and tetramethylethylenediamine (0.1 v/v %) in water for 24 hours. The sample was purified via dialysis using a 1 k molecular weight cut-off membrane with 3 water changes within 48 hours and lyophilized to isolate the final lightly-crosslinked pMPC product. The HEA/BP macroinitiator was dissolved in a water/ethanol solution (1:1 part) to prepare a 5% (w/v) solution in the presence of 2% (w/v) pMPC. The solution was mixed until homogeneous and evenly applied onto the surface of the latex using a glass pipet. The sample was immediately exposed to UV light (365 nm) for 10 minutes and then washed with water for 10 minutes and with ethanol for another 10 minutes to get rid of any excess or unreacted material from the coating. The samples were placed in an 80° C. oven for 5 minutes to evaporate the solvent. The lubricity and stability of the coating were tested by rubbing the latex coated samples for 30 seconds with distilled water.

Example 16

Sample Preparation and Hydrophilic Coating Application Using Macroinitiator HEA/BP (10% (w/v)) and PVP (0.1% (w/v))

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 10% (w/v) solution. Another solution was prepared in a similar manner containing the HEA/BP macroinitiator 10% (w/v) and PVP (MW 360 k) 0.1% (w/v). The solutions were mixed until homogeneous and evenly applied onto the surface of the latex using a glass pipet. The samples were immediately exposed to UV light (365 nm) for 15 minutes and then washed with water for 20 minutes and with ethanol for another 20 minutes to get rid of any excess or unreacted material from the coating. The samples were placed in an 80° C. oven for 5 minutes to evaporate the solvent. The lubricity and stability of the coating were tested by rubbing the latex coated samples for 30 seconds with distilled water.

Example 17

Sample Preparation, Hydrophilic Coating Application, and SEM Images of Coated Latex Sheets Using Macroinitiator AA/BP (5% (w/v)) and PVP (2% (w/v))

Figure 4:
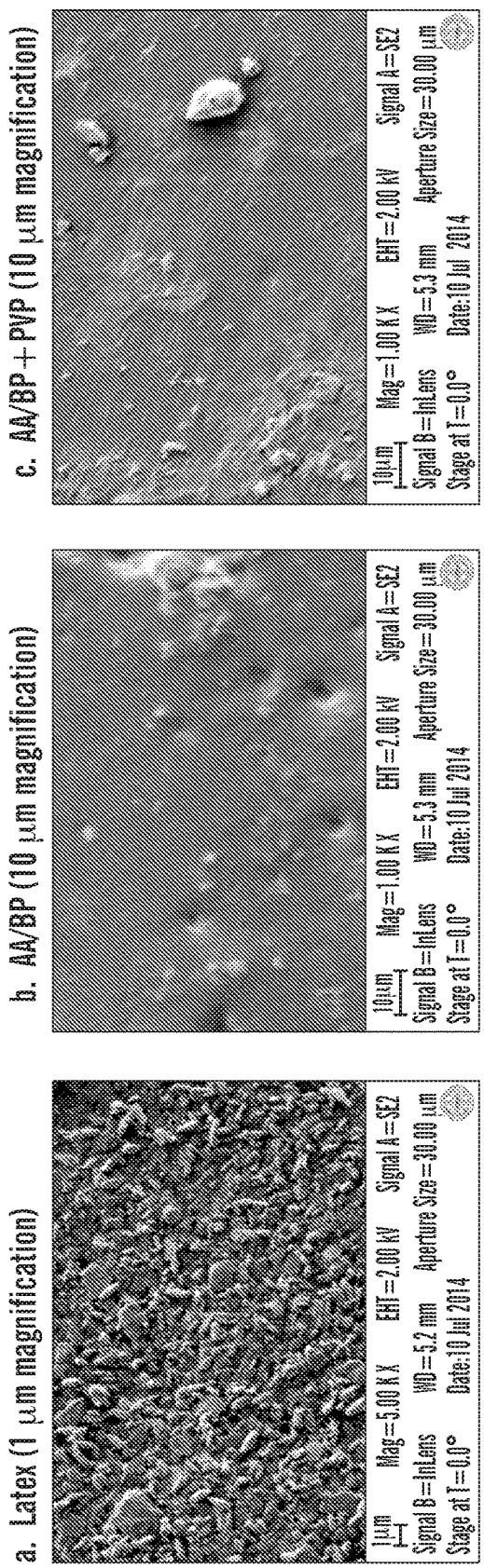
FIGS. 4A-4C show SEM images depicting latex samples with and without treatment of the hydrophilic coating at 1 μm or 10 μm magnification.

A sheet of latex was washed with water and ethanol, air-dried for 10 minutes, cut into 2×0.5 inch pieces, and mounted on glass slides. The AA/BP macroinitiator was dissolved in a water/ethanol solution (1:1 part) to prepare a 5% (w/v) solution. Another solution was prepared in a similar manner containing the AA/BP macroinitiator 5% (w/v) and PVP (MW 360 k) 2% (w/v). A small amount of 1 M sodium hydroxide was added to the solution sample containing the AA/BP macroinitiator and PVP to prevent hydrogen bonding and aggregation between the two linear polymers. The solutions were mixed until homogeneous and evenly applied onto the surface of the latex using a glass pipet. The samples were immediately exposed to UV light (365 nm) for 10 minutes and then washed with water for 10 minutes and with ethanol for another 10 minutes to get rid of any excess or unreacted material from the coating. The samples were placed in an 80° C. oven for 5 minutes to evaporate the solvent. The coated latex samples were carefully removed from the glass slide, cut into 1×1 cm sections, and mounted on SEM stubs covered in copper tape. SEM images were obtained at 10 µm and 1 µm magnification to observe the latex surface with and without the coatings (FIG. 4).

Example 18

Sample Preparation, Hydrophilic Coating Application, and Contact Angle Measurement of Coated Latex Sheets Using Macroinitiator HEA/BP (5% (w/v)) and PVP (2% (w/v)) with Varying UV Exposure Time A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 5% (w/v) solution in the presence of 2% (w/v) PVP (MW 360 k). The solution was mixed until homogeneous and evenly applied onto the surface of the latex using a glass pipet. The samples were immediately exposed to UV light (365 nm) for 0, 1, 5, or 10 minutes to investigate the minimal UV exposure time period that will result in a stable coating. Samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of each sample was measured (n=3) to determine the hydrophilicity of the surface as noted in Table 2.

TABLE 2

Contact angle measurement of coated latex samples of HEA/BP 5% (w/v) with PVP 2% (w/v) at varying UV exposure time (n = 3)

| UV Exposure Time | Contact Angle |
| --- | --- |
| 10 mins | 82.3 ± 5.7 |
| 5 mins | 79.2 ± 8.5 |
| 1 min | 111.4 ± 8.7 |
| 0 min | 103.4 ± 7.0 |

Example 19

Sample Preparation, Hydrophilic Coating Application, and Contact Angle Measurement of Coated Latex Sheets Using Macroinitiator AA/BP (5% (w/v)) and PVP (2% (w/v)) with Varying UV Exposure Time A sheet of latex was washed with water and ethanol, air-dried for 10 minutes, cut into 2×0.5 inch pieces, and mounted on glass slides. The AA/BP macroinitiator was dissolved in a water/ethanol solution (1:1 part) to prepare a 5% (w/v) solution in the presence of 2% (w/v) PVP (MW 360 k). A small amount of 1 M sodium hydroxide was added to the solution sample containing the AA/BP macroinitiator and PVP to prevent hydrogen bonding and aggregation between the two linear polymers. The solution was mixed until homogeneous and evenly applied onto the surface of the latex using a glass pipet. The samples were immediately exposed to UV light (365 nm) for 0, 1, 5, or 10 minutes to investigate the minimal UV exposure time period that will result in a stable coating. Samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of each sample was measured (n=3) to determine the hydrophilicity of the surface as noted in Table 3.

TABLE 3

Contact angle measurement of coated latex samples of AA/BP 5% (w/v) with PVP 2% (w/v) at varying UV exposure time (n = 3)

| UV Exposure Time | Contact Angle |
| --- | --- |
| 10 mins | 47.5 ± 8.5 |
| 5 mins | 48.4 ± 15.1 |
| 1 min | 82.3 ± 4.1 |
| 0 min | 52.2 ± 11.2 |

Example 20

Sample Preparation, Hydrophilic Coating Application, and Contact Angle Measurement of Coated Latex Sheets Using Macroinitiator HEA/BP (2% (w/v)) and PEG (2% (w/v))

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 2% (w/v) solution in the presence of 2% (w/v) PEG (MW 3.5 k). The solution was mixed until homogeneous and evenly applied onto the surface of the latex using a glass pipet. The samples were immediately exposed to UV light (365 nm) for 5 minutes and samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of the sample was measured (n=3) to be 46.6±11.1.

Example 21

Sample Preparation, Hydrophilic Coating Application, and Contact Angle Measurement of Coated Latex Sheets Using Macroinitiator AA/BP (2% (w/v)) and PEG (2% (w/v))

A sheet of latex was washed with water and ethanol, air-dried for 10 minutes, cut into 2×0.5 inch pieces, and mounted on glass slides. The AA/BP macroinitiator was dissolved in a water/ethanol solution (1:1 part) to prepare a 2% (w/v) solution in the presence of 2% (w/v) PEG (MW 3.5 k). The solution was mixed until homogeneous and evenly applied onto the surface of the latex using a glass pipet. The samples were immediately exposed to UV light (365 nm) for 5 minutes and samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of the sample was measured (n=3) to be 29.9±7.4.

Example 22

Sample Preparation, Hydrophilic Coating Application, and Contact Angle Measurement of Coated Latex Sheets Using Macroinitiator HEA/BP (2% (w/v)) and pMPC (2% (w/v))

A sheet of latex was washed with water and ethanol, air-dried for 10 minutes, cut into 2×0.5 inch pieces, and mounted on glass slides. Lightly cross-linked pMPC was prepared prior to solution preparation by incubation of MPC (5 w/v %), ethylene glycol dimethacrylate (1 mol/mol % of MPC), ammonium persulfate (0.005 w/v %), and tetramethylethylenediamine (0.1 v/v %) in water for 24 hours. The sample was purified via dialysis using a 1 k molecular weight cut-off membrane with 3 water changes within 48 hours and lyophilized to isolate the final lightly-crosslinked pMPC product. The HEA/BP macroinitiator was dissolved in a water/ethanol solution (1:1 part) to prepare a 2% (w/v) solution in the presence of 2% (w/v) pMPC. The solution was mixed until homogeneous and evenly applied onto the surface of the latex using a glass pipet. The samples were immediately exposed to UV light (365 nm) for 5 minutes and samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of the sample was measured (n=3) to be 23.0±5.0.

Example 23

Sample Preparation, Hydrophilic Coating Application, and Contact Angle Measurement of Coated Latex Sheets Using Macroinitiator HEA/BP (2% (w/v)) and pMPC (2% (w/v))

A sheet of latex was washed with water and ethanol, air-dried for 10 minutes, cut into 2×0.5 inch pieces, and mounted on glass slides. Lightly cross-linked pMPC was prepared prior to solution preparation by incubation of MPC (5 w/v %), ethylene glycol dimethacrylate (1 mol/mol % of MPC), ammonium persulfate (0.005 w/v %), and tetramethylethylenediamine (0.1 v/v %) in water for 24 hours. The sample was purified via dialysis using a 1 k molecular weight cut-off membrane with 3 water changes within 48 hours and lyophilized to isolate the final lightly-crosslinked pMPC product. The AA/BP macroinitiator was dissolved in a water/ethanol solution (1:1 part) to prepare a 2% (w/v) solution in the presence of 2% (w/v) pMPC. The solution was mixed until homogeneous and evenly applied onto the surface of the latex using a glass pipet. The samples were immediately exposed to UV light (365 nm) for 5 minutes and samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. The contact angle of the sample was measured (n=3) to be 19.9±4.8.

Example 24

Sample Preparation, Hydrophilic Coating Application, and Coating Thickness Measurement Using Macroinitiator HEA/BP (5% (w/v)) with PVP (2% (w/v)) and Macroinitiator AA/BP (5% (w/v)) with PVP (2% (w/v))

A sheet of latex was washed with water and ethanol, air-dried for 10 minutes, cut into 2×0.5 inch pieces, and mounted on glass slides. The HEA/BP macroinitiator was dissolved in a water/ethanol solution (1:1 part) to prepare a 5% (w/v) solution in the presence of 2% (w/v) PVP (MW 360 k). A second solution was prepared with the AA/BP macroinitiator dissolved in a water/ethanol solution (1:1 part) to prepare a 5% (w/v) solution in the presence of 2% (w/v) PVP (MW 360 k). A small amount of 1 M sodium hydroxide was added to the solution sample containing the AA/BP macroinitiator and PVP to prevent hydrogen bonding and aggregation between the two linear polymers. The solution was mixed until homogeneous and evenly applied onto the surface of the latex using a glass pipet. The samples were immediately exposed to UV light (365 nm) for 5 or 10 minutes and samples were then washed in a water/ethanol mixture (1:1 part) for 5 minutes wash any excess or unreacted material from the coating. The samples were placed in a hood and left overnight to dry. The lubricity and stability of the coating were tested by rubbing the latex coated samples for 30 seconds with distilled water. To measure the thickness of the coating, the coated latex samples were gently removed from the slide. A handheld micrometer was used to measure the thickness of the latex with and without the coating and the measurements are noted in Table 4.

TABLE 4

Coating thickness of coated latex samples of AA/BP 5% (w/v) with PVP 2% (w/v) and HEA/BP 5% (w/v) with PVP 2% (w/v)

|  | Coating (mm) | No Coating (mm) | Difference (mm) |
|---|---|---|---|
| AA/BP (5% (w/v)) + PVP (2% (w/v)) 10 minute UV exposure | 0.081 | 0.077 | 0.004 |
| HEA/BP (5% (w/v)) + PVP (2% (w/v)) 5 minute UV exposure | 0.071 | 0.068 | 0.003 |

Example 25

Sample Preparation, Hydrophilic Coating Application Using Macroinitiator HEA/BP (5% (w/v)) with PVP (2% (w/v)) and Macroinitiator AA/BP (5% (w/v)) with PVP (2% (w/v)) and Diffusion Testing to Detect Pores or Damage of Latex A sheet of latex was washed with water and ethanol, air-dried for 10 minutes, cut into 2×1 inch pieces, and mounted on glass slides. The HEA/BP macroinitiator was dissolved in a water/ethanol solution (1:1 part) to prepare a 5% (w/v) solution in the presence of 2% (w/v) PVP (MW 360 k). A second solution was prepared with the AA/BP macroinitiator dissolved in a water/ethanol solution (1:1 part) to prepare a 5% (w/v) solution in the presence of 2% (w/v) PVP (MW 360 k). A small amount of 1 M sodium hydroxide was added to the solution sample containing the AA/BP macroinitiator and PVP to prevent hydrogen bonding and aggregation between the two linear polymers. The solution was mixed until homogeneous and evenly applied onto the surface of the latex using a glass pipet. The samples were immediately exposed to UV light (365 nm) for 10 minutes and samples were then washed in a water/ethanol mixture (1:1 part) for 5 minutes wash any excess or unreacted material from the coating. The samples were placed in a hood and left overnight to dry.

Figure 3:
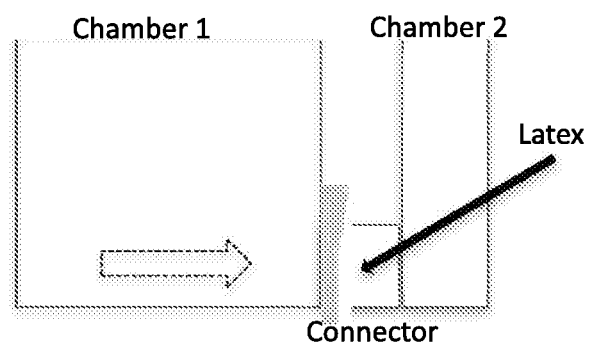
FIG. 3 shows a schematic of an exemplary setup used to perform diffusing testing to determine the presence of pores or any damage inflicted onto the latex samples after treatment of the hydrophilic coating. Chamber 1 holds a volume of about 40 mL while chamber 2 holds a smaller volume of about 1.5 mL. Stir bars are located in both chambers, which are constantly stirring throughout the study. Coated or non-coated latex samples are placed between the connector and chamber 1. Chamber 1 is filled with a FITC-dextran solution while chamber 2 is filled with water.

To determine whether the coating application or UV exposure imposed any damage to the latex, a diffusion test was performed using an apparatus described in FIG. 3. Chamber 1 was filled with 30 mL of a FITC-dextran standard (MW 19 kDa) at 0.5 mg/mL concentration dissolved in distilled water and chamber 2 was filled with 1 mL of distilled water. Latex samples, both coated and non-coated were placed between the two chambers at the connecting point to serve as a barrier between the two chambers. Stir bars were placed in both chambers and aliquots were taken from chamber 2 at varying time points up to 24 hours and refilled with distilled water. Fluorescence signal from the aliquots were measured at $\lambda_{ex}$=490 nm and $\lambda_{em}$=520 nm and compared to a standard curve of known FITC-dextran concentrations to detect any presence of FITC-dextran from chamber 1 diffusing into chamber 2 through the latex barrier. Fluorescein sodium salt was not detected in chamber 2 after 24 hours suggesting that both non-coated and coated latex samples were be effective barriers and damage to the latex was not detected (Tables 5 and 6).

TABLE 5

FITC-Dextran Standards and fluorescence signal (n = 3)

| | Concentration (ug/mL) | | | | |
|---|---|---|---|---|---|
| | 500 | 50 | 5 | 0.5 | 0 |
| Fluorescence Signal (n = 3) | 3274.29 ± 156.23 | 679.93 ± 99.92 | 80.32 ± 6.81 | 13.67 ± 1.78 | 7.95 ± 2.12 |

TABLE 6

Fluorescence reading at 0, 1, 16, and 24 hours to detect pores or damage of treated latex samples in comparison to non-coated samples (n = 3)

| | 0 Hours | 1 Hour | 16 Hours | 24 Hours |
|---|---|---|---|---|
| Non-coated latex sample | 9.21 ± 0.70 | 8.78 ± 1.22 | 8.78 ± 1.47 | 13.00 ± 3.42 |
| Latex samples coated with HEA/BP 5% (w/v) and PVP 2% (w/v) | 9.14 ± 0.87 | 11.73 ± 2.01 | 15.60 ± 2.04 | 11.12 ± 3.51 |
| Latex samples coated with AA/BP 5% (w/v) and PVP 2% (w/v) | 8.43 ± 2.14 | 7.62 ± 1.31 | 7.84 ± 0.93 | 11.55 ± 1.62 |

Example 26

Sample Preparation, Hydrophilic Coating Application, and Cytotoxicity Testing of Latex Coated Samples Using Macroinitiator HEA/BP (5% (w/v)) with PVP (2% (w/v)) and Macroinitiator AA/BP (5% (w/v)) with PVP (2% (w/v))

To determine whether the hydrophilic coatings on latex or the macroinitiators stimulate any cytotoxic effects, a colormetric trans-well cell viability test was performed using 24 well plates using an NIH/3T3 fibroblast cell-line (ATCC). This also determined whether there are components leaching from the coating when submersed in solution that would cause any adverse effects to cell viability.

A sheet of latex was washed with water and ethanol, air-dried for 10 minutes, cut into 2×1 inch pieces, and mounted on glass slides. The HEA/BP macroinitiator was dissolved in a water/ethanol solution (1:1 part) to prepare a 5% (w/v) solution in the presence of 2% (w/v) PVP (MW 360 k). A second solution was prepared with the AA/BP macroinitiator dissolved in a water/ethanol solution (1:1 part) to prepare a 5% (w/v) solution in the presence of 2% (w/v) PVP (MW 360 k). A small amount of 1 M sodium hydroxide was added to the solution sample containing the AA/BP macroinitiator and PVP to prevent hydrogen bonding and aggregation between the two linear polymers. The solution was mixed until homogeneous and evenly applied onto the surface of the latex using a glass pipet. The samples were immediately exposed to UV light (365 nm) for 5 minutes and samples were then washed in a water/ethanol mixture (1:1 part) for 5 minutes wash any excess or unreacted material from the coating. The samples were placed in a hood and left overnight to dry. The latex samples were carefully removed from the glass slide, cut into 1 cm×1 cm sections, and placed in sterile transwell plates.

Figure 5:
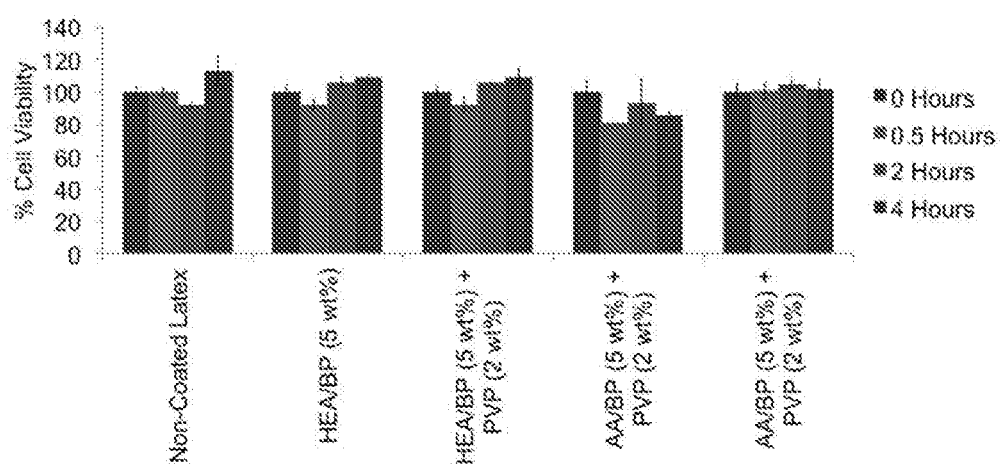
FIG. 5 depicts results from the transwell colormetric MTS cell viability assay used to test the cytotoxicity of the hydrophilic coatings on latex using NIH 3T3 fibroblast cells. Latex samples were placed into transwell, which were then incubated with the cells at 0, 0.5, 2, or 4 hours. All experiments were performed at n=3 and error bars represent the standard deviation of the mean. Results indicated that the hydrophilic coating and latex did not induce any cytotoxic effects to the cells.

NIH 3T3 fibroblast cells were cultured in DMEM media supplemented with 10% bovine calf serum and 1% L-glutamine-penicillin-streptomycin and maintained at 37° C. in 5% $CO_2$ with humidity. When the cells reached 80% to 90% confluency, they were split at a 1:4 ratio using a standardized trypsin-based detachment. To determine cytotoxicity, cells were seeded at 100 000 cells/well in 12-well plates and incubated overnight at 37° C. The media was removed and washed with PBS before incubating cells with the transwells containing the coated or noncoated latex samples for 0, 0.5, 2, or 4 hours in media. An in vitro cell viability assay was performed using a standard MTS proliferation assay protocol (CellTiter 96® Aqueous One, Promega, Madison, Wis.). Absorbance was recorded at 492 nm with a multi-plate reader and cell viability was calculated in relation to control cells (FIG. 5).

Example 27

Sample Preparation and Hydrophilic Coating Application Using Macroinitiator HEA/BP (5% (w/v)) with PVP (2% (w/v)) to Coat a Latex Male Condom Via Dipcoating The HEA/BP macroinitiator was dissolved in a water/ethanol solution (1:1 part) to prepare a 5% (w/v) solution in the presence of 2% (w/v) PVP (MW 360 k) to prepare a 400 mL solution and was mixed until homogeneous. A non-lubricated male latex condom was unrolled onto a glass penile-shaped mold that has a diameter of 4 cm and a length of 20 cm and the latex was washed with water and ethanol and dried prior to the hydrophilic coating treatment. The mold with the unrolled latex condom was dipped into the homogenous 400 mL solution and carefully raised so that a thin, even layer of the solution was observed on the latex surface. The mold was immediately placed onto a rotary apparatus. The coated sample rotated at 45 rotations per minute while the coated latex condom was exposed to UV light (365 nm) for 5 minutes. The coated latex sample was then washed in a water/ethanol mixture (1:1 part) for 5 minutes to wash any excess or nonreacted material from the coating. The coated latex condom was placed back on the rotation apparatus in which the device rotated at 45 rotations per minute and left to air-dry for 20 minutes before assessing the coating.

Example 28

Sample Preparation and Hydrophilic Coating Application Using Macroinitiator AA/BP (5% (w/v)) with PVP (2% (w/v)) to Coat a Latex Male Condom Via Dipcoating The AA/BP macroinitiator was dissolved in a water/ethanol solution (1:1 part) to prepare a 5% (w/v) solution in the presence of 2% (w/v) PVP (MW 360 k) to prepare a 400 mL solution and was mixed until homogeneous. A small amount of 1 M sodium hydroxide was added to the solution sample containing the AA/BP macroinitiator and PVP to prevent hydrogen bonding and aggregation between the two linear polymers. A non-lubricated male latex condom was unrolled onto a glass penile-shaped mold that has a diameter of 4 cm and a length of 20 cm and the latex was washed with water and ethanol and dried prior to the hydrophilic coating treatment. The mold with the unrolled latex condom was dipped into the homogenous 400 mL solution and carefully raised so that a thin, even layer of the solution was observed on the latex surface. The mold was immediately placed onto a rotary apparatus. The coated sample rotated at 45 rotations per minute while the coated latex condom was exposed to UV light (365 nm) for 5 minutes. The coated latex sample was then washed in a water/ethanol mixture (1:1 part) for 5 minutes to wash any excess or nonreacted material from the coating. The coated latex condom was placed back on the rotation apparatus in which the device rotated at 45 rotations per minute and left to air-dry for 20 minutes before assessing the coating.

Example 29

Apparatus Set-Up to Determine the Coefficient of Friction (COF) Via Sled Configuration A rectangular latex sample (approximately 1 inch wide by 8 inches long) was washed with water and ethanol and adhered to a large immobilized base via cyanoacrylate adhesive. A black rubber stopper was selected as the articulating counter-surface due to its moderate conformability. A small amount of water was added onto the surface of the latex using a pipette. The stopper was placed at one end of the rectangular latex sample and dragged by hand at a steady velocity via a load cell attached to the stopper by a string with negligible plasticity.

The COF is equal to the ratio of the frictional force to the normal force of the stopper (obtained via a balance). This force was determined by measuring the force required to slide the rubber stopper "sled" which is equal magnitude to the frictional force opposing the sled's motion under constant velocity. COF values were determined under initial articulation conditions (i.e. averaged over the duration of a single slide over the 8-inch long sample) as well as under cyclically repeated articulation to determine cycle-dependence of COF for various hydrophilic latex coatings and for non-coated latex.

Example 30

COFs Among Latex Surfaces Coated with HEA/BP (5% Wt) with or without PVP (2% Wt) and in Comparison to Non-Coated Latex Under Lubrication by Water COFs were determined via sled configuration as described previously. Latex was washed, prepared, and coated with a solution prepared with the HEA/BP (5% wt) macroinitiator with or without PVP (2% wt) as described previously. The COF of black rubber against latex coated with HEA/BP with PVP under lubrication by water and under a normal force of 0.677 kPa was 0.819.

The COF of black rubber against latex coated with HEA/BP without PVP under the same conditions was 1.02. The COF of black rubber against non-coated latex under the same conditions was 1.07, which was 31% greater than that of the latex sample coated with HEA/BP and PVP.

Example 31

Apparatus Set-Up to Determine the COF Via a Multi-Axial Dynamic Mechanical Analysis Instrument Latex, which was previously washed and dried, was adhered via cyanoacrylate adhesive to a 12-mm diameter ultra high molecular weight polyethylene cylindrical substrate. The polyethylene cylinder was placed into a fixture mounted to the servomotor of a BOSE Electroforce 3200 dynamic mechanical analysis instrument. In a series of tests, a fixed amount of commercially available lubricant or water was pipetted on top of the latex sample. In another series of tests, a glass chamber was filled with a commercially available lubricant or water to surround the latex sample. A 7-mm diameter polyurethane cylindrical specimen was selected as the articulating counter-surface due to its moderate conformability (durometer hardness of 40 A, "medium soft"). The polyurethane specimen was loaded axially into a fixture mounted to a load and torque cell, and the desired normal force between the latex and polyurethane specimen was obtained by controlling the displacement of the two surfaces. Conformation of the two surfaces was confirmed visually via observation of no light penetrating within the interface of the two surfaces upon illumination by a flashlight. Upon establishing the desired normal force, the latex surface was rotated against the polyurethane specimen at a desired angular velocity.

Figure 6:
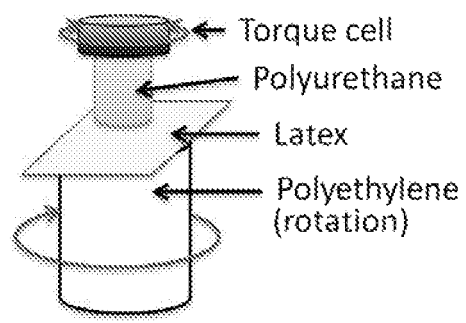
FIG. 6 shows a schematic of the configuration of fixtures and sample for COF determination by multi-axial dynamical mechanical analysis.

The COF is equal to the ratio of the frictional force to the normal force on the latex (as measured by the load cell). This frictional force refers to the opposing force to the latex surface when in motion which is equal to the torque in the system as measured by the torque cell under this constant velocity as depicted in FIG. 6. The COF values were determined under initial articulation conditions (i.e. over one full rotation of the polyethylene substrate) as well as under cyclically repeated articulation to determine cycle-dependence of COF as well as time-dependence of COF for hydrophilic latex coatings as well as for non-coated latex and their associated lubrication by various fluid lubricants.

Example 32

Figure 7:
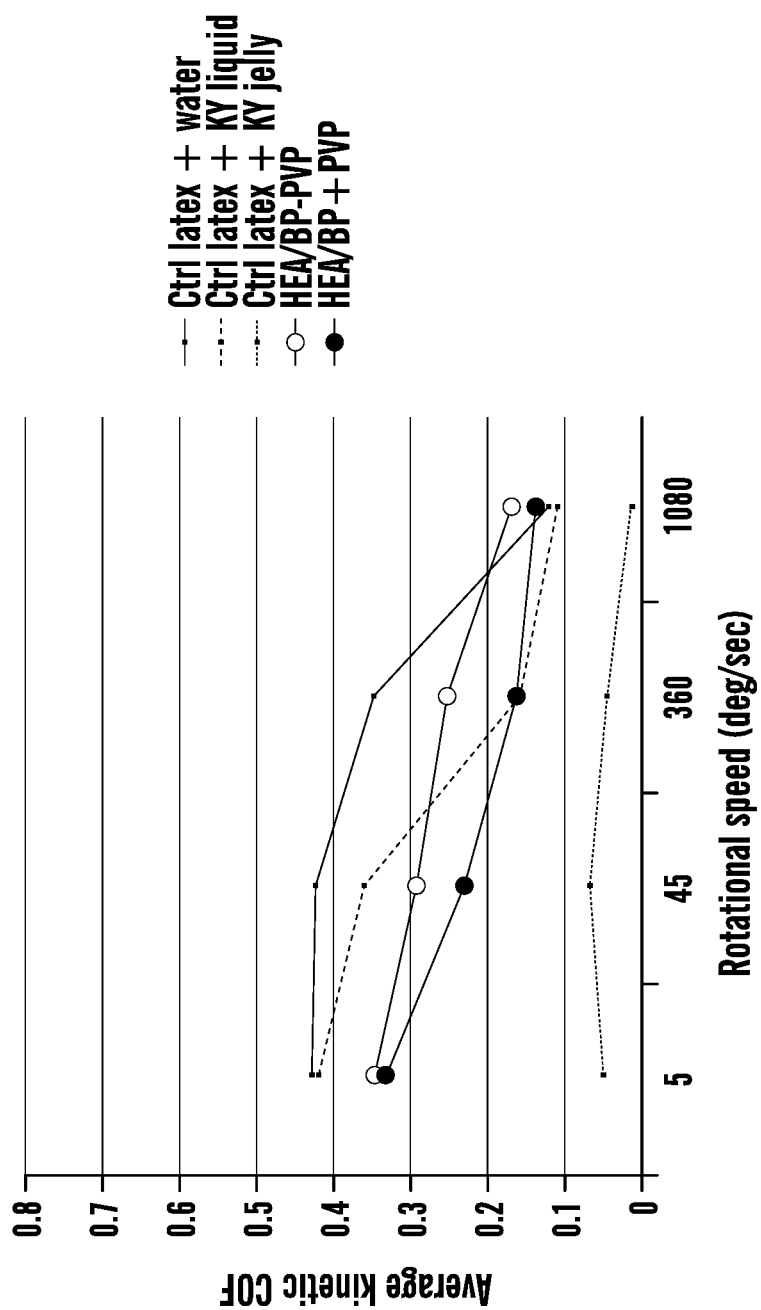
FIG. 7 shows coefficients of friction (COFs) of polyurethane against latex coated with HEA/BP with and without PVP under lubrication by water and non-coated latex under lubrication by water, KY® Liquid, and KY® Jelly under a normal compressive load of 3 N and various sliding velocities (specified as rotational speed in degrees/sec, where 1 rotation i.e. 360°/sec equates with 22 mm/sec). Non-coated latex is abbreviated as "ctrl latex;" presence or absence of PVP is abbreviated by (+) or (−) sign, respectively.

Comparison of COFs Among Latex Coated with HEA/BP (5% Wt) with or without PVP (2% Wt) Under Lubrication by Water and Non-Coated Latex Under Lubrication by Water, KY® Liquid, and KY® Jelly COFs were determined via multi-axial dynamic mechanical analysis instrument as described previously. Latex was washed, prepared, and coated with the solution composed of the HEA/BP (5% wt) macroinitiator with or without PVP (2% wt) as described previously. The COFs of polyurethane against latex coated with HEA/BP with and without PVP under lubrication by water and non-coated latex under lubrication by water, KY® Liquid (Water, glycerin, sorbitol, propropylene glycol, hydroxyethylcellulose, benzoic acid, methyl paraben, sodium hydroxide), and KY® Jelly (Water, glycerin, hydroxythylcellulose, chlorhexidine, gluconate, gluconolactone, methyl paraben, sodium hydroxide) under a range of multiple sliding velocities and a normal compressive load of 3 N are shown in FIG. 7.

The general trend observed when comparing COF values from highest COF to lowest COF, is summarized by non-coated latex lubricated by water~latex coated with HEA/BP without PVP lubricated by water>non-coated latex lubricated by KY® Liquid~latex coated with HEA/BP with PVP lubricated by water>non-coated latex lubricated by KY® Jelly.

Example 33

Figure 8:
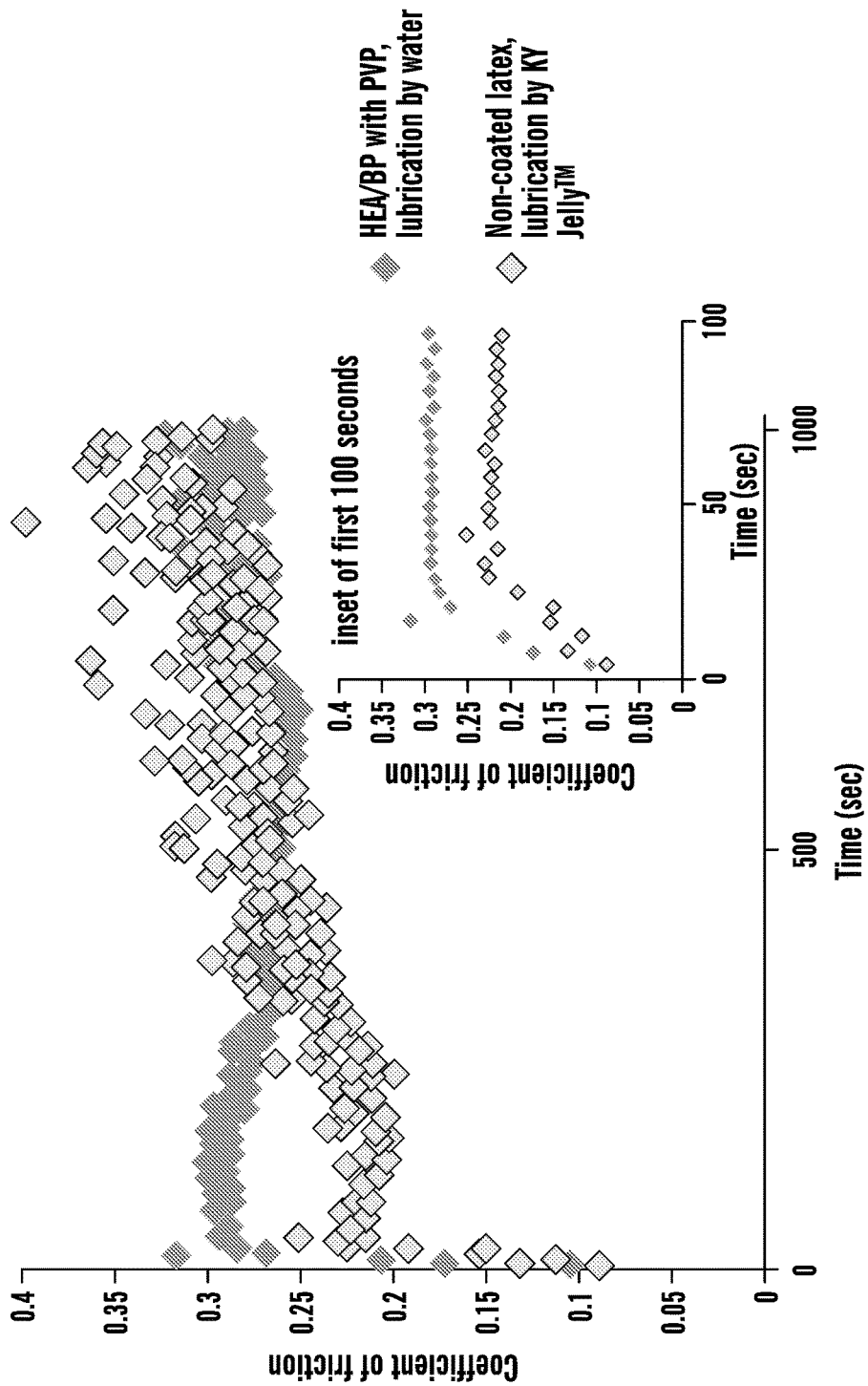
FIG. 8 shows COFs over repeated torsion between latex coated by HEA/BP with PVP under lubrication by water and non-coated latex under lubrication by KY® Jelly.

Comparison of COFs Over Repeated Torsional Articulation Between Latex Coated by HEA/BP with PVP Under Lubrication by Water and Non-Coated Latex Under Lubrication by KY® Jelly COFs were determined via multi-axial dynamic mechanical analysis instrument as described previously. Latex was washed, prepared, and coated with the solution composed of the HEA/BP (5% wt) macroinitiator with or without PVP (2% wt) as described previously. COFs over sequential cycles of torsional articulation of polyurethane counter-surface against either latex coated with HEA/BP and PVP under lubrication by water or non-coated latex under lubrication by KY® Jelly, with both configurations under a normal force of 230 kPa, are shown in FIG. 8. Specifically, the sequential cycling was composed of a repeating pattern of two rotations clockwise followed by two rotations counter-clockwise at a sliding velocity of 22 mm/sec, for a duration of 1000 seconds, corresponding to 1000 rotations.

COFs of non-coated latex under lubrication by KY® Jelly and of coated latex under lubrication by water both reached initial equilibrium values at approximately the same time of 30 seconds after beginning the cyclically repetitive friction test. At this time, COF of non-coated latex under lubrication by KY® Jelly was approximately 0.22, while COF of coated latex under lubrication by water was approximately 0.29. Over the duration of remaining approximately 970 seconds of the test, the COF values of non-coated latex under lubrication by KY® Jelly increased by approximately 50% from about 0.22 to about 0.33, whereas the COF of coated latex under lubrication by water showed negligible increase. The final COF values for non-coated latex under lubrication by KY® Jelly was approximately 14% greater than that for coated latex under lubrication by water. Both COF-vs-time profiles for each of the two configurations tested experienced a minimum in COF values in between the initial equilibrium at 30 seconds and the final time point of 1000 seconds; due to this local minimum in COF values, the COF of non-coated latex under lubrication by KY® Jelly fluctuated over a range of magnitude equal to approximately 55% of its initial COF, where the COF of coated latex under lubrication by water fluctuated over a range of magnitude equal to approximately 17% of its initial COF-approximately 3.2 times lesser than the non-coated sample. The inventors hypothesize that this difference is due to sloughing off of KY® Jelly in the configuration of the non-coated latex, whereas the hydrated boundary lubrication imparted by the coating layer of the coated latex experiences negligible sloughing over the time course (1000 seconds) and cycle history (1000 cycles) studied.

Example 34

Figure 9A:
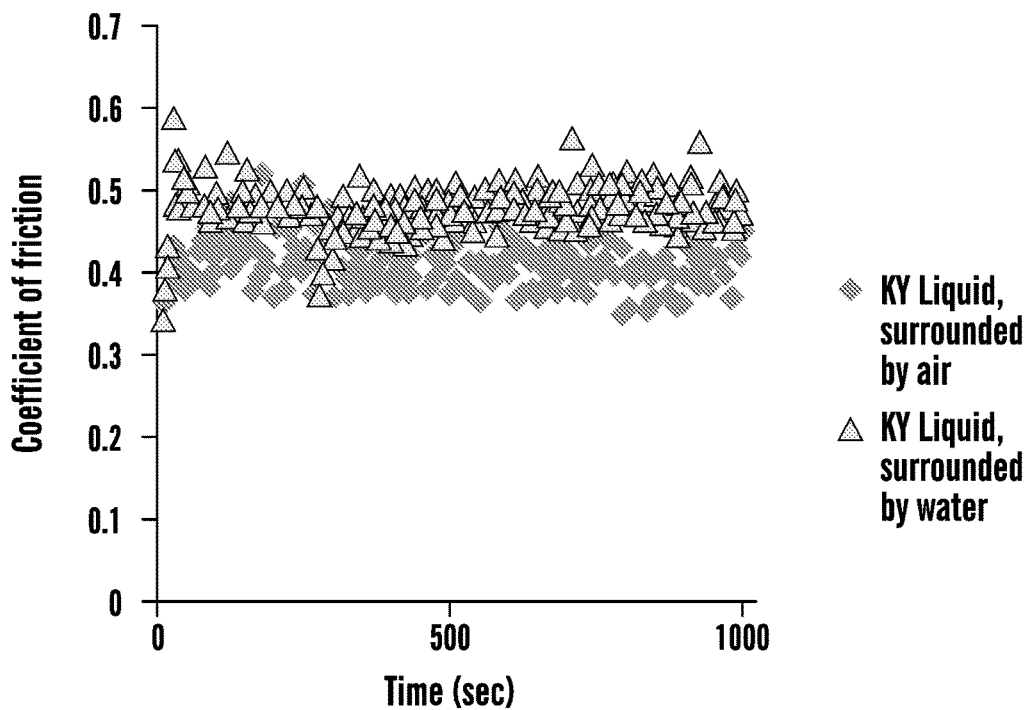
FIGS. 9A-9B shows COFs over repeated torsion between non-coated latex under lubrication by KY® Liquid surrounded by air and surrounded by water.
Figure 9B:
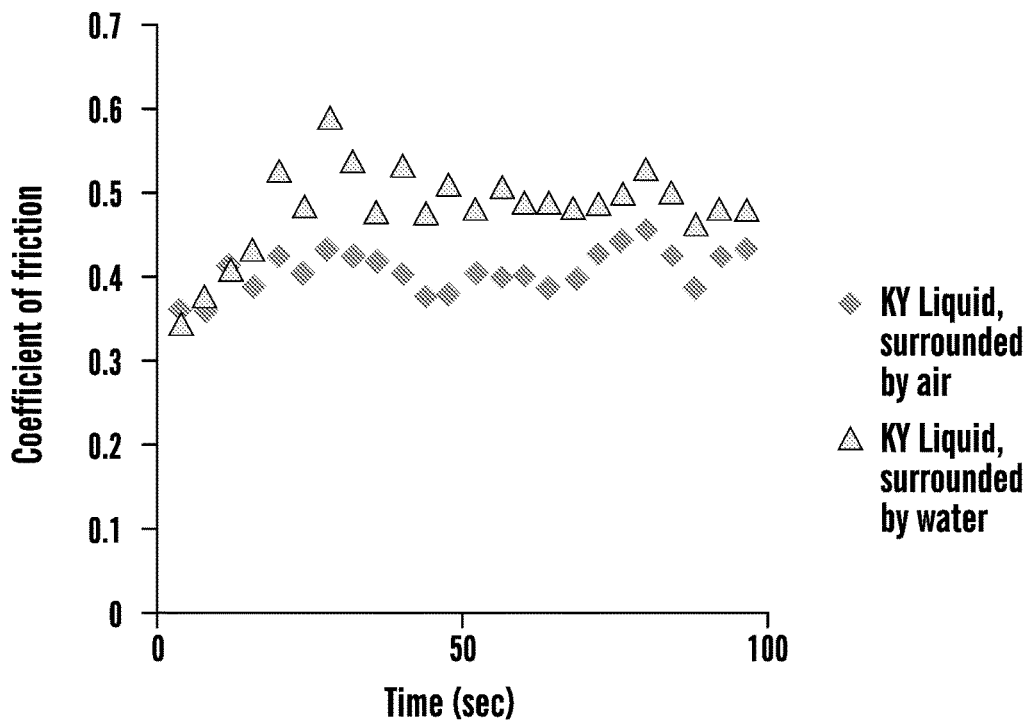

Comparison of COFs Over Repeated Torsional Articulation Between Non-Coated Latex Under Lubrication by KY® Liquid Surrounded by Air and Surrounded by Water COFs were determined via multi-axial dynamic mechanical analysis instrument as described previously. COFs over sequential cycles of torsional articulation of polyurethane counter-surface against non-coated latex under a stress of 230 kPa and under lubrication by KY® Liquid surrounded by either air or water are shown in FIG. 9. The configuration of KY® Liquid surrounded by air represents a physiologically-relevant scenario of personal lubricant sloughing off from the articulating areas, while the configuration of KY® Liquid surrounded by water represents a physiologically-relevant scenario of personal lubricant being diluted by bodily fluids.

COFs of non-coated latex under lubrication by KY® Liquid surrounded by either air or water both reached initial equilibrium values at approximately the same time of 30 seconds after beginning the cyclically repetitive friction test. At this time, COF when surrounded by air was approximately 0.4, while COF when surrounded by water was approximately 0.5, or about 25% greater. In the full time scale of the test (1000 seconds), these COF values of approximately 0.4 and 0.5 for COF when KY® Liquid was surrounded by either air or water, respectively, maintain steady equilibria for the duration of testing.

Example 35

Figure 10:
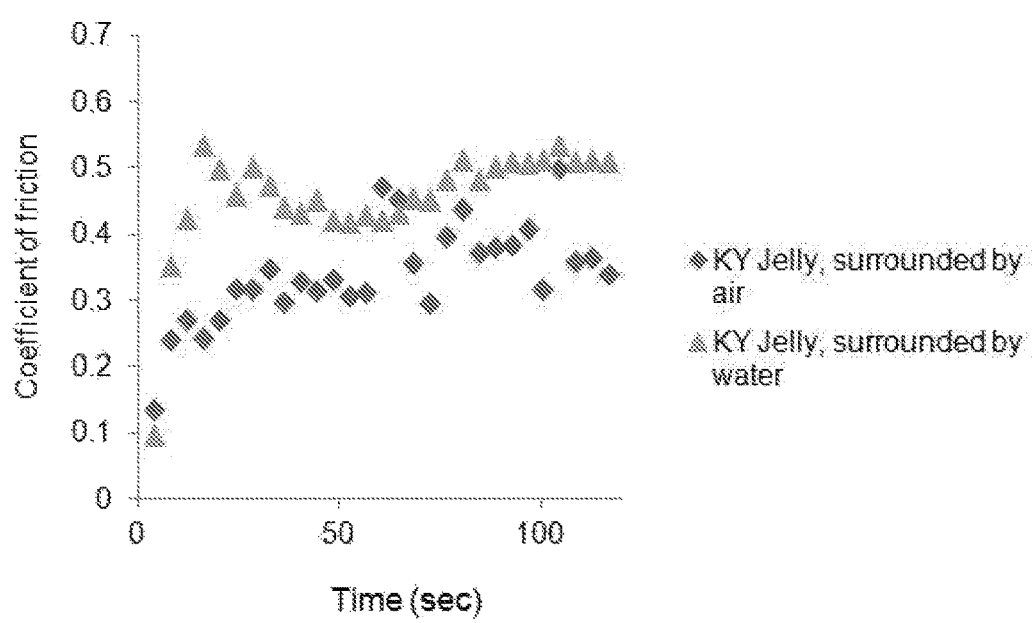
FIG. 10 shows COFs over repeated torsion between non-coated latex under lubrication by KY® Jelly surrounded by air and surrounded by water.

Comparison of COFs Over Repeated Torsional Articulation Between Non-Coated Latex Under Lubrication by KY® Jelly Surrounded by Air and Surrounded by Water COFs were determined via multi-axial dynamic mechanical analysis instrument as described previously. COFs over sequential cycles of torsional articulation of polyurethane counter-surface against non-coated latex under a stress of 104 kPa and under lubrication by KY® Jelly surrounded by either air or water are shown in FIG. 10. The configuration of KY® Jelly surrounded by air represents a physiologically-relevant scenario of personal lubricant sloughing off from the articulating areas, while the configuration of KY® Jelly surrounded by water represents a physiologically-relevant scenario of personal lubricant being diluted by bodily fluids.

COFs of non-coated latex under lubrication by KY® Jelly surrounded by either air or water both reached initial equilibrium values at approximately the same time of 30 seconds after beginning the cyclically repetitive friction test. At this time, COF when surrounded by air was approximately 0.35, while COF when surrounded by water was approximately 0.5, or about 43% greater.

In regards to results reported from the previous example, the COF values increased when the articulation between polyurethane and non-coated latex, lubricated by either KY® Liquid or KY® Jelly, was surrounded by water compared to when surrounded by air. We hypothesize that the fluid lubricants KY® Liquid and KY® Jelly are dissolved in the surrounding water bath, and the fact that equilibrium COF values were reached after about 30 seconds of articulation may indicate that the fluid lubricants only provide COF-lowering effect for the first 30 seconds of articulation. In comparison, the coated latex samples described in previous examples function irrespective of a large surrounding bath of water, as the lubricating material is covalently bound to the latex and does not dissolve into the water over time or with repeated articulation.

Example 36

Figure 11:
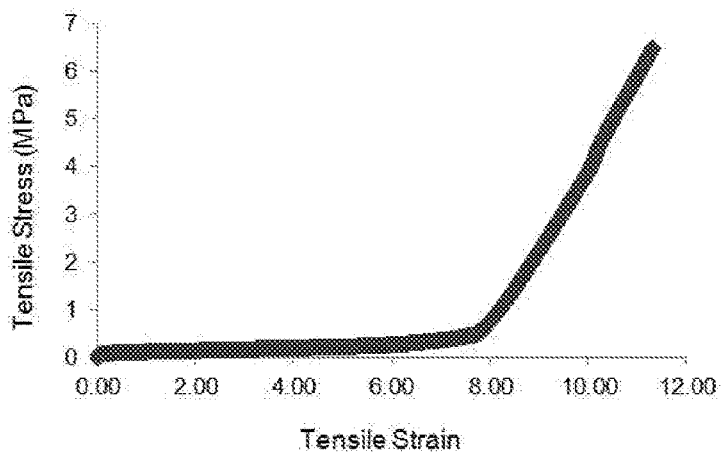
FIG. 11 shows typical stress-strain plot tensile testing of non-coated latex at a constant strain rate of 0.5/sec.

Determination of Uniaxial Tensile Properties Via Uniaxial Dynamic Mechanical Analysis Instrument Rectangular latex strips of 1 cm in width and 8 cm in length were either not coated or coated with hydrophilic polymer as described previously, soaked in water for approximately 5 seconds, and mounted with clamps on an Instron tensile testing apparatus. The samples were stretched at a strain rate of 0.5/sec, while a load cell recorded the measured tensile force which was converted to tensile stress using the cross sectional area of the latex strips (determined via calipers as described previously). Tensile stress was plotted against tensile strain; a typical plot is shown in FIG. 11. Tensile testing of latex typically reveals two linear regions in the stress-strain curve: a low-strain tensile modulus, $E_{\varepsilon<5}$, corresponding to the elastic modulus for strain values under 5, and a high-strain tensile modulus, $E_{\varepsilon>5}$, that engages typically when tensile strain reaches about 6-10, immediately prior to tensile failure. (Failure is not shown in the exemplary plot in FIG. 13.)

Example 37

Figure 12:
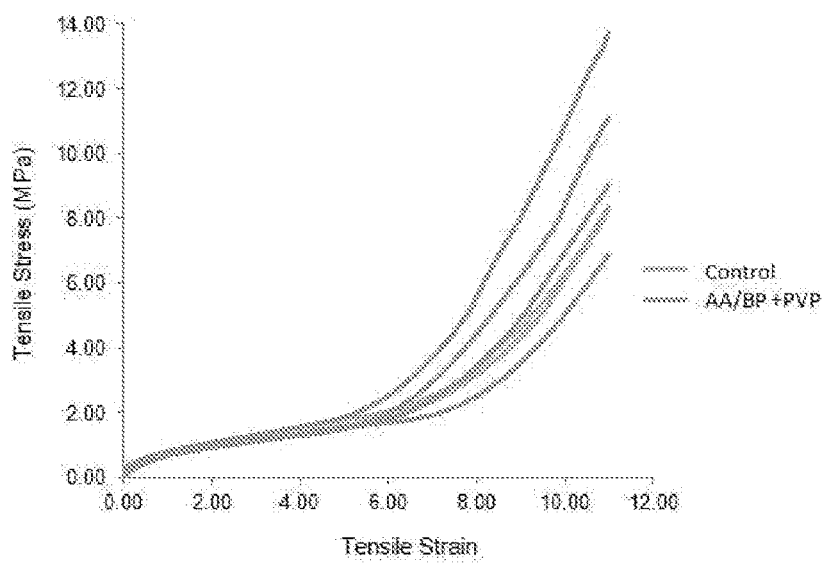
FIG. 12 shows stress-strain plots for individual samples of non-coated latex (control) and latex coated with AA/BP and PVP.

Comparison of Tensile Moduli $E_{\varepsilon<5}$ and $E_{\varepsilon>5}$ for Non-Coated Latex and Latex Coated with AA/BP and PVP Tensile moduli were determined via uniaxial dynamic mechanical analysis instrument as described previously. Latex was coated with macroinitiator AA/BP and PVP as described previously. Stress vs strain data, indicative of $E_{\varepsilon<5}$ and $E_{\varepsilon>5}$, are shown in FIG. 12 for non-coated latex and latex coated with AA/BP and PVP.

Testing revealed similar stress responses for both non-coated and coated latex specimens when subjected to identical strain profiles. In both the first and second phases of low magnitude and high magnitude rate of change in stress as strain was linearly increased ($E_{\varepsilon<5}$ and $E_{\varepsilon>5}$, respectively), Example 38

Latex Touch-Test Survey with Latex Sheets Coated with Macroinitiator AA/BP (5% (w/v)) with PVP (2% (w/v)), Latex Sheets Lubricated with KY Liquid®, and Non-Lubricated Latex Sheets Sheets of latex were washed with water and ethanol, air-dried for 10 minutes, cut into 2×0.5 inch pieces, and mounted on glass slides. The HEA/BP macroinitiator was dissolved in a water/ethanol solution (1:1 part) to prepare a 5% (w/v) solution in the presence of 2% (w/v) PVP (MW 360 k). A second solution was prepared with the AA/BP macroinitiator dissolved in a water/ethanol solution (1:1 part) to prepare a 5% (w/v) solution in the presence of 2% (w/v) PVP (MW 360 k). The solution was mixed until homogeneous and evenly applied onto the surface of the latex using a glass pipet. The samples were immediately exposed to UV light (365 nm) for 5 or 10 minutes and samples were then washed in a water/ethanol mixture (1:1 part) for 5 minutes wash any excess or unreacted material from the coating. The samples were placed in a hood and left overnight to dry.

A touch-test survey was designed to determine whether human subjects are able to feel and distinguish the difference in slipperiness between coated latex samples, non-lubricated latex samples, and latex samples lubricated with a commercially available lubrication. A latex touch-test was administered to a population sample representing a variety of ages, ethnicities, levels of education, and degrees of sexual activity and condom use. Participants were asked to feel and compare three samples before and after submergence in and removal from water (to represent physiological fluid during intercourse): 1) non-lubricated latex, 2) latex lubricated by 50 uL of KY Liquid®, and 3) latex treated with the AA/BP (5% (w/v)) and (2% (w/v)) coating.

33 participants were asked to rate each sample on a 7-point scale, with 1-point representing most sticky and 7 points representing most slippery. Following exposure to water, latex samples coated with the AA/BP and PVP coating underwent a statistically significant increase in slipperiness of 2.76 points up to a slipperiness rating of 6.24 points, while latex samples lubricated by KY Liquid® decreased in slipperiness by 1.15 points down to a rating of 4.85 points. After exposure to water, our coating was statistically significantly more slippery than latex lubricated by KY Liquid®. 85% participants agreed that latex samples treated with the AA/BP and PVP coating were the most slippery by touch in comparison to the three samples. Within these 85% participants, 70% of these participants felt our coating was "much" or "very much" more slippery than the other two tested latex samples.

Statistically significant differences (95% confidence level) were identified through ANOVA with Tukey-Kramer Multiple Comparisons using a Bonferroni correction.

Example 39

Sample Preparation and Coating Application of AA/BP (5% (w/v)) with PVP (2% (w/v)) and HEA/BP (5% (w/v)) with PVP (2% (w/v)) for Atomic Force Microscopy (AMF) Characterization of the Surface Topology and Roughness of Coated and Non-Coated Latex A sheet of latex was washed with water and ethanol, air-dried for 10 minutes, cut into 20×20 mm pieces, and mounted on 22×22 mm glass slides. The AA/BP macroinitiator was dissolved in a water/ethanol solution (1:1 part) to prepare a 5% (w/v) solution along with PVP (MW 360 k) 2% (w/v). The solutions were mixed until homogeneous and evenly applied onto the surface of the latex using a glass pipet. The HEA/BP (5% (w/v) and PVP (2% (w/v)) solution was also prepared and applied onto latex samples in a similar manner. The samples were immediately exposed to UV light (365 nm) for 10 minutes and then washed with an ethanol and water mixture for 5 minutes to remove any excess or unreacted material from the coating. The samples were left at room temperature under a constant airflow overnight to evaporate the solvent.

Atomic force microscopy experiments were performed using a Molecular Force Probe-3D instrument (MFP-3D, Asylum Research, CA) to obtain height and lateral force profiles simultaneously, which were then followed by subsequent normal force spectroscopy. The rectangular silicon nitride probe (MLCT, Bruker, CA) used in these studies had a nominal diameter of 20 nm. The spring constant was determined to be ~20 pN/nm in both air and water, using the thermal tuning method. The lateral sensitivity was determined to be 80-120 pN/mV using the wedge calibration method. The frictional coefficient between silicon nitride and wafer was determined to be 0.17 in air and 0.20 in water. The normal load was initially set at 5 nN during the lateral scan. The topological profile was performed on a 20×20 µm² area of non-coated and coated latex samples. The scanning rate was 1 Hz yielding a sliding velocity of 50 µm/s. Roughness of the surface was determined by the root-mean-square variation on the surface across a 20×20 µm² area (n>3).

Figure 13C:
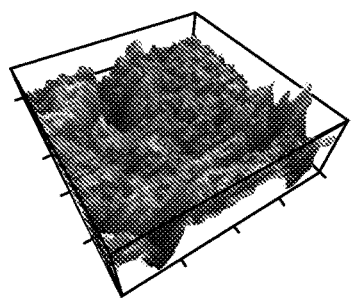
Figure 13C:
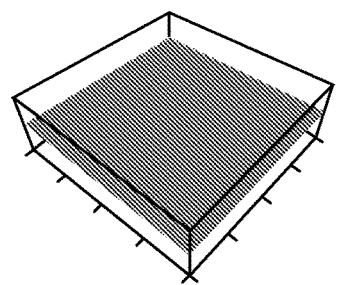
Figure 13C:
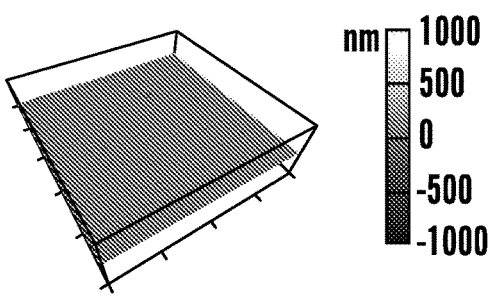

Three-dimensional AFM images of the topography of the non-coated and coated latex sheets in air are shown in FIG. 13. The surface of non-coated latex samples (FIG. 13A) shows sub-micron roughness with an rms value of 275±31 nm. In contrast, the AMF images depicted coated latex samples to have different nanotopological profiles and smoother surfaces, consistent with our SEM analysis and observations from FIG. 2. Latex samples coated with either the HEA/BP and PVP (FIG. 13B) or AA/BP and PVP (FIG. 13C) depicted a smooth and homogenous surface with rms values of 8.2±1.5 nm and 3.1±0.5 nm, respectively.

Example 40

Sample Preparation and Coating Application of AA/BP (5% (w/v)) with PVP (2% (w/v)) and HEA/BP (5% (w/v)) with PVP (2% (w/v)) for Friction Comparison of Coated and Non-Coated Latex Using AFM Solutions and latex samples were prepared and the coatings were applied in a similar manner as previously described. Atomic force microscopy experiments were performed in a similar manner as previously described. The frictional force profiles were performed on a 20×20 µm² area of non-coated and coated latex samples. The scanning rate was 1 Hz yielding a sliding velocity of 50 µm/s. The height and frictional force profiles were collected simultaneously in contact mode on the direction perpendicular to the cantilever length to maximize tip bending. The lateral force resulted in positive values during trace (left to right) while negative values were obtained during retrace (right to left). The frictional force was determined by the difference in lateral force in trace and retrace divided by two. After scans were conducted in air, samples incubated in water for 15 min prior the topology and force measurement in deionized filtered water (20 nm filter). To compare the potential fields near polymer surface between air and water, normal force spectroscopy was performed immediately after imaging to minimize potential errors associated with systematic drift.

To compare frictional coefficients of non-coated and coated latex samples with 5% w/v HEA/BP or AA/BP with 2% w/v of PVP, lateral force microscopy was conducted to obtain lateral force profiles. The normal force was determined by the sum of the normal load and adhesion forces from normal force spectroscopy. In all cases, non-coated and coated latex samples showed relatively high frictional force, even in excess of the normal load which is typically observed in AFM studies under low-load frictional conditions where intermolecular adhesion forces exceed the external normal load. However, when repeating this frictional study after submerging the latex samples in water for 15 minutes, it was found that the frictional force for all three coated latex samples was significantly reduced. Non-coated latex samples showed the greatest frictional coefficient value of 0.94±0.18 after submerging them in water, whereas the HEA/BP and PVP coated latex samples showed a superior frictionless surface with a frictional coefficient value of 0.03±0.02. Latex samples coated with AA/BP and PVP have a frictional coefficient value of 0.30±0.23. The frictional analysis measurements indicated that these hydrophilic macroinitiator coatings were able to reduce friction on latex surfaces in the presence of water. The frictional data conducted both in air and in water are noted in Table 7.

TABLE 7

AFM analysis of the frictional force profiles of non-coated and coated latex samples conducted in air and submerged in water.

| Natural Rubber Samples | Frictional Coefficient* (in air) | Frictional Coefficient** (in water) |
| --- | --- | --- |
| Non-coated | 2.87 | 0.94 ± 0.18 |
| HEA/BP and PVP | 0.06 | 0.03 ± 0.02 |
| AA/BP and PVP | 4.22 | 0.30 ± 0.23 |

*N = 1 was conducted for samples conducted in air
**N = 3 was conducted for samples conducted in water

Example 41

Advancing and Receding Contact Angle Measurements of Latex Samples Coated with HEA/BP (5% (w/v)) with PVP (2% (w/v)) and AA/BP (5% (w/v)) with PVP (2% (w/v))

To further compare the wetting properties of the latex surface, advancing and receding contact angles were measured and compared to non-coated and coated latex samples with the HEA/BP or AA/BP macroinitiator at 5% w/v with 2% w/v PVP, as noted in Table 8. Coated and non-coated latex samples were prepared in a similar manner as described. The contact angle hysteresis was noted for each sample by the difference between the advancing and receding contact angles for each sample. Latex samples coated with the AA/BP macroinitiator and PVP showed the lowest hysteresis, indicating a greater ability to wet the surface, while non-coated latex samples showed the greatest hysteresis.

TABLE 8

Advancing and receding contact angle measurements of coated and non-coated latex samples. All coated samples were prepared at 5 w/v % macroinitiator with 2 w/v % PVP. All measurements were done at n = 10 and reported in degrees.

|  | Non-coated | HEA/BP + PVP | AA/BP + PVP |
| --- | --- | --- | --- |
| Advancing Contact Angles | 100.8 ± 5.1 | 82.4 ± 7.9 | 20.3 ± 2.1 |
| Receding Contact Angles | 24.4 ± 4.8 | 26.3 ± 4.2 | 14.2 ± 2.6 |
| Contact Angle Hysteresis* | 76.4 | 56.1 | 6.1 |

*Contact angle hysteresis is measured by noting the difference between the advancing and receding contact angle measurements

Example 42

Gel Permeation Chromatography (GPC) Characterization of HEA/BP and AA/BP Macroinitiators (MW$_{THEO}$=100 k)

HEA/BP and AA/BP macroinitiators were synthesized at MW$_{THEO}$=100 k as previously described. GPC characterization of the HEA/BP and AA/BP macroinitiators were analyzed against polystyrene or poly(acrylic acid) standards DMF buffer containing 0.05M of lithium bromide and was performed using a Styragel Column, HR SE at a flow rate of 1.0 mL/min with a refractive index detector. Both macroinitiators were dissolved the GPC eluent buffer at a concentration of 6 mg/mL and filtered through a syringe filter with 0.22 μm pore size. GPC columns were purchased from Waters (Milford, Mass.). Results are listed in Table 9.

TABLE 9

HEA/BP and AA/BP Macroinitiator GPC Characterization

| Macro-initiator | Weight % of BP in macro-initiator* | MW$_{Theo}$ | MW$_{GPC}$ | M$_n$** | M$_P$ | PDI |
| --- | --- | --- | --- | --- | --- | --- |
| HEA/BP | 10.3% | 100 000 | 226 195 | 129 000 | 162 457 | 1.7 |
| AA/BP | 9.7% | 100 000 | 69 492 | 84 970 | 56178 | 1.2 |

*The weight % or BP to hydrophilic units (theoretical weight or 10 w/w %) was calculated via NMR integration of the proton peak from aromatic protons from the BP units, which was referenced against protons from the polymer backbone.
**GPC analysis in DMF against polystyrene standards for the HEA/BP macroinitiator or acrylic acid standards for the AA/BP macroinitiator.

Example 43

Contact Angle Characterization of Coated Latex Samples with 5 w/v % HEA/BP or 5 w/v % AA/BP Macroinitiator at Varying Concentrations in Solution Macroinitiator solutions were prepared and the coating application process was conducted as previously described. The contact angles of non-coated or coated latex sheets using the HEA/BP or AA/BP macroinitiator were measured using a dynamic sessile drop method with deionized water. The surface of a non-coated latex sample has a contact angle of 117.2±5.6 degrees C. When latex samples were coated with the HEA/BP or AA/BP macroinitiator, prepared at 10% w/v, in a similar manner as described with 30 minutes of UV exposure, contact angles notably decreased approximately 30 degrees, as noted in Table 10. These decreased contact angle values indicated a more hydrophilic surface than that found on non-coated latex sheets. The coating application using 5% and 2% w/v of the macroinitiators was explored to determine whether the resulting contact angle of the coating was dependent on the macroinitiator concentration. Decreasing the concentration of the macroinitiator from 10% to 2% w/v resulted in an increase in the contact angle for both macroinitiators, with the 2% w/v coated latex sheets approaching contact angles similar to that of non-coated latex sheets. Similar contact angle values were noted within the 10%, 5%, and 2% w/v concentrations groups independent of the macroinitiator used for the coating application.

TABLE 10

Contact angle measurements of latex sheets coated with the macroinitiator prepared at varying concentrations

| Macro-initiator | Solution Concentration | | |
| --- | --- | --- | --- |
|  | 10% w/v* | 5% w/v* | 2% w/v* |
| HEA/BP | 88.6 ± 1.3 | 91.5 ± 7.1 | 100.8 ± 4.7 |
| AA/BP | 83.4 ± 13.9 | 87.1 ± 2.8 | 94.4 ± 11.1 |

*Contact angle measurements were obtained at an N = 5 and reported in degrees.

Example 44

Contact Angle Measurements of Coated Latex Samples with 5 w/v % of HEA/BP or 5 w/v % of AA/BP with Different Hydrophilic Polymers at 2 w/v %

To further enhance the hydrophilicity of the coating, the inventors explored the addition of a second high molecular weight synthetic hydrophilic polymer to the coating such as poly(vinylpyrillidone) (PVP), poly(ethylene glycol) (PEG), or poly(2-methacryloyloxyethyl phosphorylcholine) (pMPC). These polymers contain a high number of repeated polar or charged functional groups along their polymer backbone. PVP is used in many applications due to its extremely low cytotoxicity, non-antigenic, and high water-soluble properties PEG also possesses hydrophilic properties and is compatible with aqueous photo-curing systems. It can be grafted onto surfaces of biomedical devices to improve their biocompatibility and reduce thrombogenicity. pMPC, which is composed of units bearing a phosphorylcholine group, is highly water soluble, biocompatible, and when coated on surfaces can afford surfaces with low friction and antibiofouling properties. pMPC is also widely used for a variety of surface fouling challenges in the medical device arena.

These hydrophilic polymers were incorporated into the coating by dissolving them in the macroinitiator solution. The HEA/BP or AA/BP macroinitiator was dissolved in solution at 5% w/v along with 2% w/v of the hydrophilic polymer. The coating solution was applied on latex samples, exposed to UV light at 365 nm for 30 minutes, and washed in a similar manner as previously described before the coating was assessed and characterized by contact angle measurements as noted in Table 11.

TABLE 11

Contact angle measurements of the coated latex samples with or without the hydrophilic polymers with the macroinitiator

| Hydrophilic Polymer | Macroinitiators | |
| --- | --- | --- |
| | HEA/BP* | AA/BP* |
| No polymer | 91.5 ± 7.1 | 87.1 ± 2.8 |
| PVP | 84.8 ± 5.6 | 32.8 ± 8.8 |
| PEG | 74.8 ± 2.4 | 29.9 ± 7.4 |
| pMPC | 27.4 ± 5.8 | 23.6 ± 5.7 |

*Contact angle measurements were obtained at an N = 5 and reported in degrees. PEG used for these studies had an $M_n$ of 20,000. All macroinitiators were prepared at 5% w/v with or without 2% w/v of the hydrophilic polymer.

Example 45

IR Characterization of Coated Latex Samples with 5% w/v of HEA/BP with pMPC or PEG Hydrophilic Polymers at 2% w/v The coating solution was applied on latex samples in a similar manner as previously described. IR spectroscopy was used to characterize the macroinitiator and hydrophilic polymer on the latex surface, exposed to UV light at 365 nm for 30 minutes, and washed in a similar manner as previously described before the coating was assessed and characterized by FT-IR as noted in FIG. 14.

Example 46

Dip-Coating Application Approach to Male Latex Condoms with 5% w/v HEA/BP and 2% w/v PVP, or with 5% w/v AA/BP and 2% w/v PVP for Passage of the "Water Leak Test" Under ISO 23409 Standards The protocol was scaled-up to apply either the 5% w/v HEA/BP and 2% w/v PVP formulation or the 5% w/v AA/BP and 2% w/v PVP hydrophilic coating onto male latex condoms using a dip-coating approach. A non-lubricated male latex condom was unrolled, washed, and dried before fitting it onto a penile-shaped glass mold. The condom was dipped into a 400 mL solution containing the macroinitiator solution and carefully raised to obtain a thin and even layer of the solution on the entire condom surface. This mold was immediately placed onto an apparatus that vertically rotated the coated latex condom at 45 rpm while being exposed to UV light for 25 min. The coated latex sample was washed in a water/ethanol mixture and dried under a steady airflow. Through this application approach, a thin, even, and stable coating resulted on the condom surface even after the washes and rubbing the coated latex condom in the presence of water.

To determine whether the coating application or UV exposure resulted in any visual defects or holes inflicted to the latex, the "Water Leak Test" was performed as described in ISO 23409 "Annex J: Testing for Holes". Five male latex condoms were coated as previously described. The latex condoms were removed from the glass mold and mounted onto an apparatus at the open end to allow 300 mL of water to fill the condom while being suspended in the air at 25° C. All five coated condoms coated with either 5% w/v HEA/BP and 2% w/v PVP, or with 5% w/v AA/BP and 2% w/v PVP did not show any signs of visible leakage when tied and rolled onto colored absorbent paper as described under the ISO, and thus passed the test.

Example 47

Synthesis of N-(4-benzoylphenyl) acrylamide

To a round-bottom flask, 4-aminobenzophenone (19.7 g, 100 mol) and triethylamine (27.5 mL, 200 mol) were added and dissolved in 200 mL of anhydrous dichloromethane. The reaction was equipped with a magnetic stirrer bar and cooled to 0° C. Acryloyl chloride (9.2 mL, 120 mol in 50 mL anhydrous dichloromethane) was added drop-wise to the mixture through an addition funnel. The reaction mixture was warmed to room temperature and stirred overnight. The mixture was washed with 0.1M hydrochloric acid, saturated sodium bicarbonate solution, and then saturated brine. The combined organic layers were dried over $Na_2SO_4$ and then concentrated in vacuum to afford a crude product. The crude product was purified by column chromatography (5:1 hexane:ethyl acetate) to yield N-(4-benzoylphenyl) acrylamide as a light yellow solid (21.5 g, yield=85.0%).

Example 48

Synthesis of the AA_2/BP Macroinitiator (Modified AA/BP Macroinitiator with AA Groups Attached to the Polymer Backbone Via an Amide Linkage), with $MW_{THEO}$ of 150 k and 10% (w/w) BP to AA The AA_2/BP macroinitiator possess acrylic acid units along the polymer chain to be attached to the polymer backbone via an amide linkage instead of an ester linkage in the AA/BP macroinitiator to prevent hydrolysis. To a round bottom flask, acrylic acid (9.4 g, 130.5 mmol, distilled under vacuum before use), N-(4-benzoylphenyl) acrylamide (0.60 g, 2.4 mmol), and 2, 2'-azobis(2-methylpropionitrile) (5.3 mg, 0.033 mmol) were dissolved in dimethylformamide (30 mL), placed in a 100 mL Schlenk tube and degassed via freeze-thaw cycles prior to the reaction. The reaction mixture was placed in an oil bath at 70° C. for 18 h. After the reaction, the polymers were dialyzed against distilled water using a 3 k MWCO dialysis tubing with a cellulose ester membrane for 24 hours with 3 water changes to remove the organic solvent and unreacted monomer. Water from the sample was removed via freeze-drying to isolate the product, a hydroscopic white solid. The macroinitiator was confirmed and characterized via ¹H-NMR. The mole percentage of benzophenone was calculated from the integration of the aromatic hydrogen atoms at δ=7.2-8.0 ppm, which was referenced against the integration of protons on the polymer backbone at δ=1.2-2.5 ppm.

Example 49

Sample Preparation and Hydrophilic Coating Application of Coated Latex Sheets Using Macroinitiator AA_2/BP (5% w/v) and PVP (2% w/v)

A sheet of latex was washed with water and ethanol, air-dried for 10 minutes, cut into 2×0.5 inch pieces, and mounted on glass slides. The AA_2/BP macroinitiator was dissolved in a water/ethanol solution (1:1 part) to prepare a 2% (w/v) solution with PVP (MW 360 k) at 2% (w/v). The solution was mixed until homogeneous and evenly applied onto the surface of the latex using a glass pipet. The sample was immediately exposed to UV light (365 nm) for 10 minutes and then washed with a water and ethanol mixture for 5 minutes to remove of any excess or unreacted materials from the coating. The samples were left at room temperature under a constant air flow overnight to evaporate the solvent. The lubricity and stability of the coating were tested by rubbing the latex coated samples for 30 seconds with distilled water.

The invention claimed is:

1. A composition comprising: a latex article having at least one layer of a hydrophilic coating, wherein the hydrophilic coating comprises a co-polymer network comprising a macroinitiating co-polymer and a hydrophilic polymer on the surface of the latex article, and wherein the macroinitiating co-polymer structure: (a) is selected from the group consisting of:

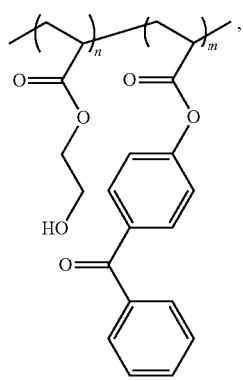

Formula A

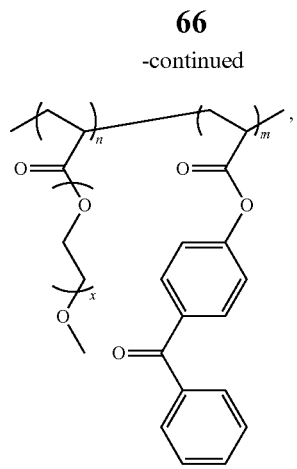

Formula B

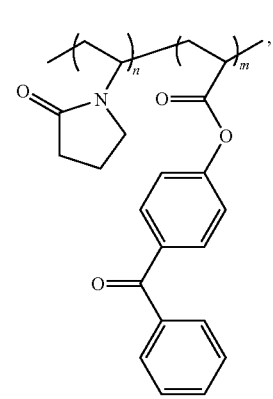

Formula C

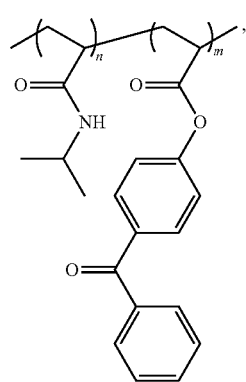

Formula D

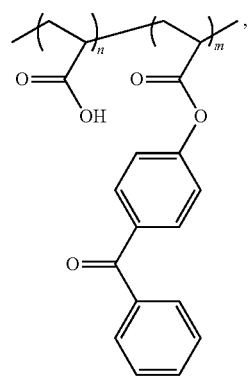

Formula E

Formula F

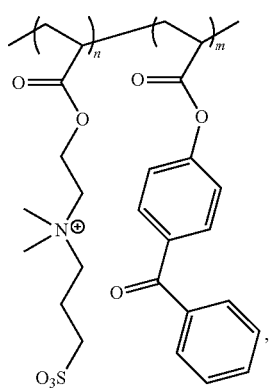
,

Formula G

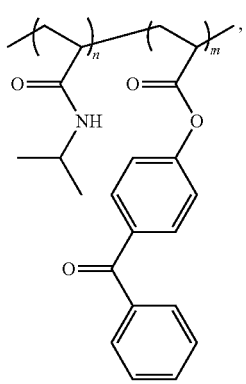
;

or (b) comprises a structure selected from the group consisting of:

Formula D

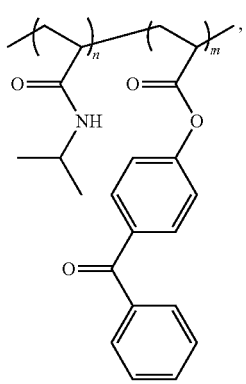

Formula F

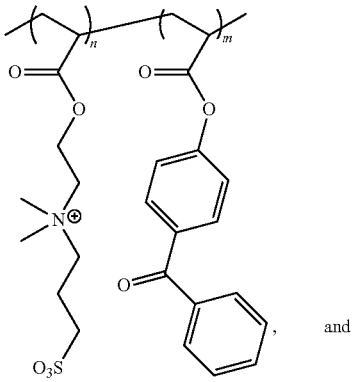
, and

Formula G

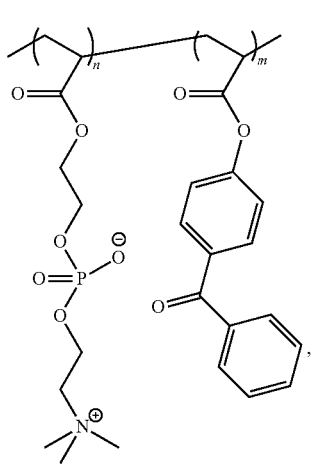
, wherein, in Formulas A-G, n and m are integers that represent the number of randomized repeat unit in which n can range from 10 to 5000 and the proportion of the monomer with the m subscript can range from 1% to 50% w/w of the monomer with the n subscript.

2. The composition of claim 1, wherein the latex article is selected from the group consisting of male condoms, female condoms, latex-based gloves, biomedical devices, sexual stimulation devices, contact lenses, rubber bands, shoes, clothing, kitchen appliances, swimwear, sportswear, sporting instruments, boats, vehicles, military devices, or toys.

3. The composition of claim 1, wherein the macroinitiating co-polymer is covalently linked to the latex article and the hydrophilic polymer is entangled within the macroinitiating co-polymer.

4. The composition of claim 1, wherein the macroinitiating co-polymer comprises a structure is selected from the group consisting of:

Formula A

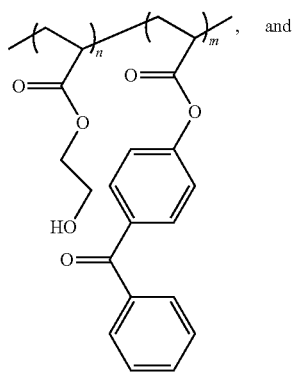

, and

Formula E

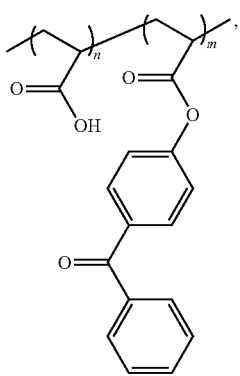

wherein:

n and m are integers that represent the number of randomized repeat unit in which n can range from 10 to 5000 and the proportion of the monomer with the m subscript can range from 1% to 50% w/w of the monomer with the n subscript.

5. The composition of claim 1, wherein the hydrophilic polymer is selected from the group consisting of

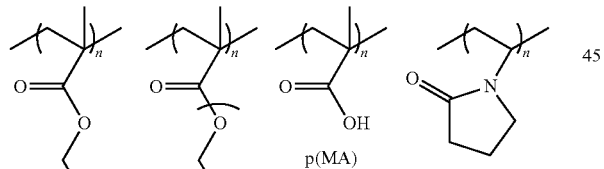

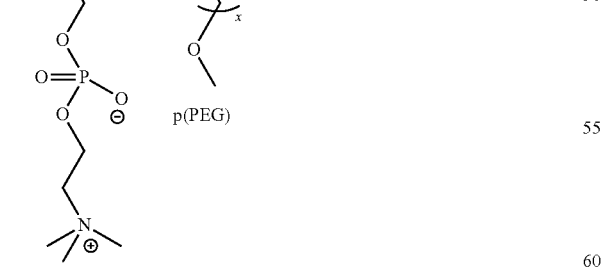

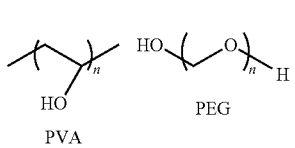

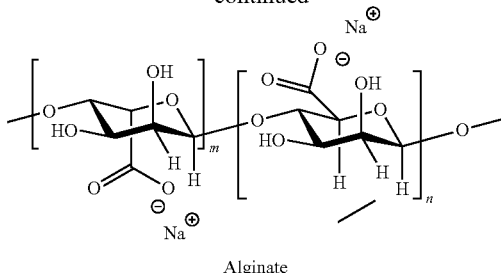

Alginate and combinations thereof.

6. The composition of claim 1, wherein the hydrophilic polymer comprises a thermoplastic polymer, a polysaccharide, or a charged hydrophilic polymer.

7. The composition of claim 1, further comprising at least one bioactive agent.

8. The composition of claim 1, wherein the hydrophilic coating is evenly distributed over the area of the latex article.

9. A method for coating a latex article with a hydrophilic coating, the method comprising: (a) contacting a latex article with a macroinitiating co-polymer and a hydrophilic polymer, (b) exposing the latex article to a light source, thereby coating the latex article with a hydrophilic coating, and wherein the macroinitiating co-polymer structure: (a) is selected from the group consisting of:

Formula A

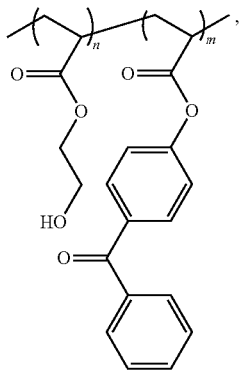

Formula B

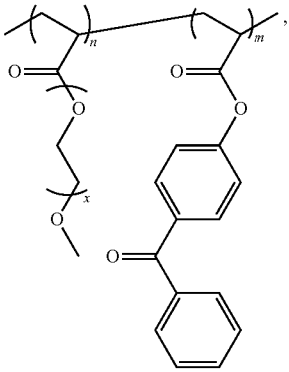

Formula C
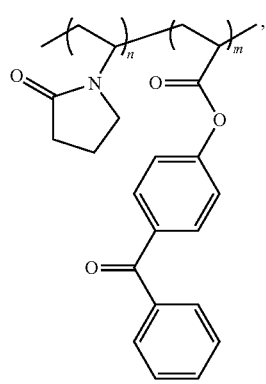
Formula D
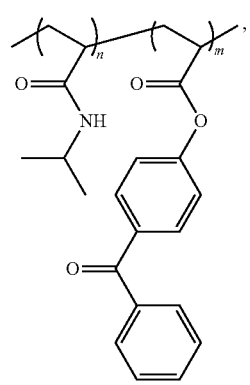
Formula E
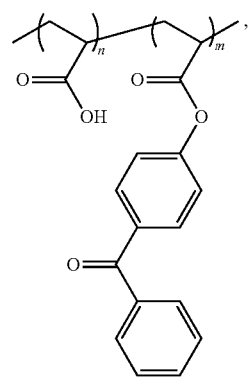
Formula F
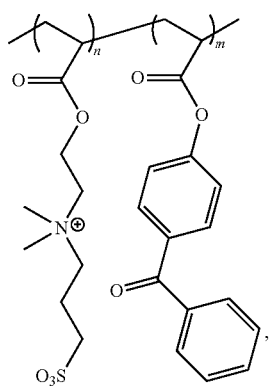
Formula G
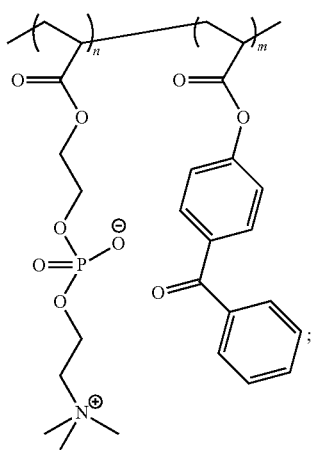
or (b) comprises a structure selected from the group consisting of:
Formula D
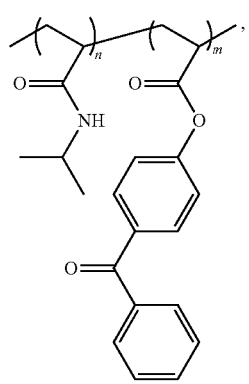
Formula F
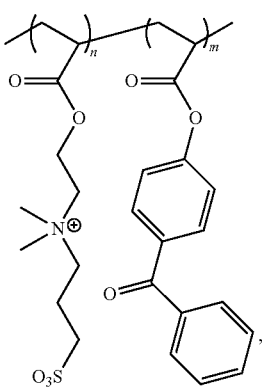
and -continued Formula G

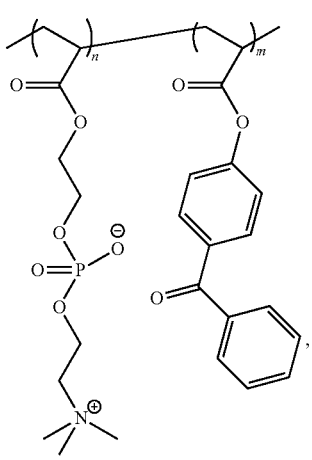

wherein:
n and m are integers that represent the number of randomized repeat unit in which n can range from 10 to 5000 and the proportion of the monomer with the m subscript can range from 1% to 50% w/w of the monomer with the n subscript.

10. The method of claim 9, wherein the macroinitiating co-polymer is covalently linked to the latex article and the hydrophilic polymer is entangled within the acroinitiating co-polymer.

11. The method of claim 9, wherein the macroinitiating co-polymer comprises a Formula structure selected from the group consisting of Formula A

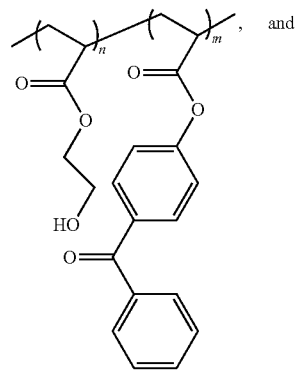, and

Formula E

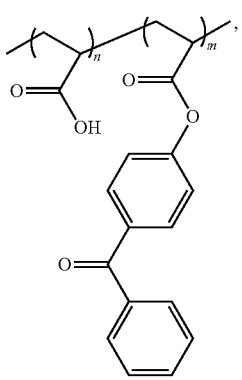, wherein:
n and m are integers that represent the number of randomized repeat unit in which n can range from 10 to 5000 and the proportion of the monomer with the m subscript can range from 1% to 50% w/w of the monomer with the n subscript.

12. The method of claim 9, wherein the hydrophilic polymer is selected from the group consisting of

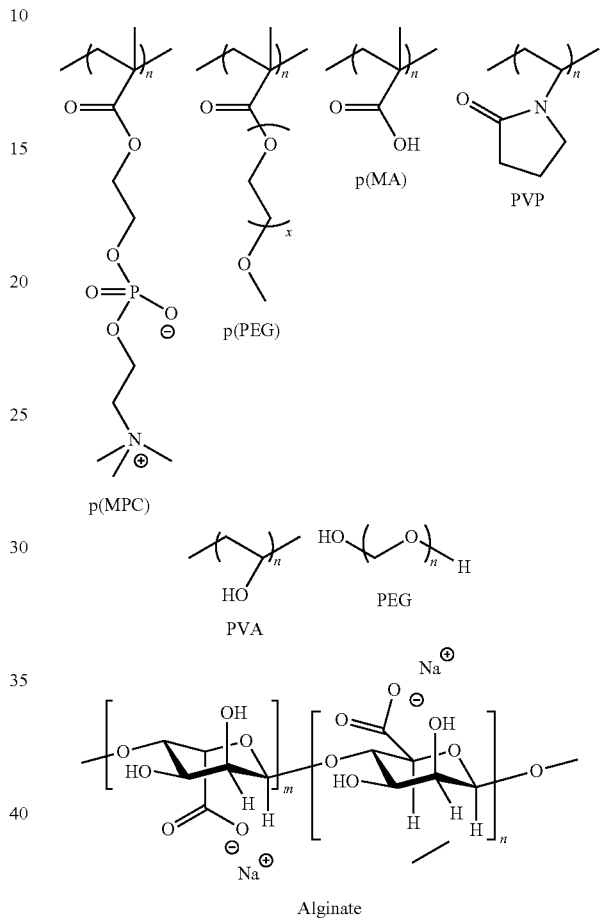

and combinations thereof.

13. The method of claim 9, further comprising a bioactive agent.

14. The method of claim 9, wherein the hydrophilic coating is evenly distributed over the area of the latex article.

15. The method of claim 9, wherein the macroinitiating polymer is synthesized via a polymerization reaction.

16. The method of claim 15, wherein the polymerization reaction is initiated by a free radical initiator selected from the group consisting of an azo compound, an organic peroxide, an inorganic peroxide, and a redox initiating system.

17. The method of claim 15, wherein the polymerization reaction is performed at a temperature between 75-100° C.

18. The method of claim 9, wherein the macroinitiating copolymer and the hydrophilic polymer are applied to the latex article via a spraying method.

19. The method of claim 15, wherein the polymerization reaction is a traditional free radical reaction, atom transfer radical polymerization, reversible addition-fragmentation chain transfer polymerization, cationic polymerization, or anionic polymerization.

* * * * *